United States Patent
Norcini et al.

(10) Patent No.: US 10,106,629 B2
(45) Date of Patent: Oct. 23, 2018

(54) MULTIFUNCTIONAL ACYLPHOSPHINE OXIDE PHOTOINITIATORS

(71) Applicant: IGM RESINS ITALIA S.R.L., Milan (IT)

(72) Inventors: Gabriele Norcini, Comabbio (IT); Marika Morone, Lipomo (IT); Andrea Bernini Freddi, Gavirate (IT); Giuseppe Li Bassi, Gavirate (IT); Giovanni Floridi, Novara (IT)

(73) Assignee: IGM RESINS ITALIA S.R.L., Milan (IT)

( * ) Notice: Subject to any disclaimer, the term of this patent is extended or adjusted under 35 U.S.C. 154(b) by 45 days.

(21) Appl. No.: 15/314,147

(22) PCT Filed: May 28, 2015

(86) PCT No.: PCT/EP2015/061910
§ 371 (c)(1),
(2) Date: Nov. 28, 2016

(87) PCT Pub. No.: WO2015/181332
PCT Pub. Date: Dec. 3, 2015

(65) Prior Publication Data
US 2017/0240659 A1   Aug. 24, 2017

(30) Foreign Application Priority Data

May 30, 2014 (IT) .............................. VA2014A0017

(51) Int. Cl.
| | |
|---|---|
| *C08F 2/50* | (2006.01) |
| *C08F 2/46* | (2006.01) |
| *C07F 9/32* | (2006.01) |
| *C07F 9/36* | (2006.01) |
| *G03F 7/029* | (2006.01) |
| *G03F 7/038* | (2006.01) |
| *C09D 11/101* | (2014.01) |
| *C09D 11/107* | (2014.01) |
| *C09D 11/38* | (2014.01) |
| *G03F 7/004* | (2006.01) |

(52) U.S. Cl.
CPC .............. *C08F 2/50* (2013.01); *C07F 9/3229* (2013.01); *C07F 9/3252* (2013.01); *C07F 9/3258* (2013.01); *C07F 9/36* (2013.01); *C09D 11/101* (2013.01); *C09D 11/107* (2013.01); *C09D 11/38* (2013.01); *G03F 7/029* (2013.01); *G03F 7/038* (2013.01); *G03F 7/0045* (2013.01)

(58) Field of Classification Search
CPC ......... C08F 2/50; C09D 11/38; C09D 11/107; C09D 11/101; C07F 9/3258; C07F 9/3229; C07F 9/36

USPC ............. 522/27, 7, 6, 71, 189, 184, 1; 520/1
See application file for complete search history.

(56) References Cited

U.S. PATENT DOCUMENTS

| | | | |
|---|---|---|---|
| 3,844,916 A | 10/1974 | Gaske | |
| 4,136,055 A | 1/1979 | Lyons | |
| 4,950,581 A | 8/1990 | Koike et al. | |
| 5,013,768 A | 5/1991 | Kiriyama et al. | |
| 5,482,649 A | 1/1996 | Meixner et al. | |
| 5,734,002 A | 3/1998 | Reich et al. | |
| 6,296,986 B1 | 10/2001 | Illsley et al. | |
| 7,166,647 B2 | 1/2007 | Herlihy et al. | |
| 7,354,957 B2 | 4/2008 | Herlihy | |
| 2012/0046376 A1* | 2/2012 | Loccufier | C08F 2/50 522/34 |

FOREIGN PATENT DOCUMENTS

| | | |
|---|---|---|
| AU | 2003205731 A1 | 9/2003 |
| DE | 19700064 | 7/1997 |
| DE | 10206117 | 8/2003 |
| EP | 0245639 | 11/1987 |
| EP | 0280222 | 8/1988 |
| EP | 0438123 | 7/1991 |
| EP | 0445624 | 9/1991 |
| EP | 0678543 | 10/1995 |
| EP | 1616921 A1 | 1/2006 |
| EP | 1674499 A1 | 6/2006 |
| GB | 2180358 | 3/1987 |
| GB | 2348644 | 10/2000 |
| IT | 102012902094539 | 4/2014 |
| WO | 0010972 | 3/2000 |
| WO | 0026219 | 5/2000 |
| WO | WO2004103580 A1 | 12/2004 |
| WO | WO2006056541 A1 | 6/2006 |
| WO | 2012062692 | 5/2012 |
| WO | 2013164394 | 11/2013 |
| WO | 2014095724 | 6/2014 |

OTHER PUBLICATIONS

Search Report and Written Opinion from Italian parent application ITVA20140017 dated Sep. 24, 2014.
International Search Report from related application PCT/EP2015/061910 dated Aug. 19, 2015.
Written Opinion of the International Search Authority from related application PCT/EP2015/061910 dated Aug. 19, 2015.

(Continued)

*Primary Examiner* — Jessica Whiteley

(57) ABSTRACT

The present invention relates to a series of novel multifunctional mono- and bis-acylphosphine oxides, which are useful as photoinitiators, and to photocurable compositions comprising said photoinitiators.

11 Claims, No Drawings

(56) References Cited

OTHER PUBLICATIONS

Corrales et al "Free radical macrophotoinitiators: an overview on recent advances" Journal of Photochemistry and Photobiology A: Chemistry 159 (2003) 103-114.
Yu Chen et al, "Novel Multifunctional Polymeric Photoinitiators and Photo-Coinitiators Derived from Hyperbranched Polyglycerol", Macromol. Chem. Phys. 208, 2007, 1694-1706.

* cited by examiner

MULTIFUNCTIONAL ACYLPHOSPHINE OXIDE PHOTOINITIATORS

RELATED APPLICATIONS

This application is a US national phase application of international application number PCT/EP2015/061910, filed 28 May 2015, which designates the US and claims priority to Italian Application No. VA2014A000017 filed 30 May 2014, the contents of each of which are hereby incorporated by reference as if set forth in their entireties.

TECHNICAL FIELD

The present invention relates to multifunctional mono- and bis-acylphosphine oxides, which are useful as photoinitiators, and to photocurable compositions comprising said photoinitiators.

PRIOR ART

Radiation curable compositions are used in many industries including, but not limited to, coatings for various substrates such as concrete, metal, ceramic, glass, plastic, composites and textiles. The curing of the composition is accomplished by photoinitiators, which absorb the UV energy and react to generate free radicals, which in turn react with double bonds in the composition (e.g., acrylate groups) to form new free radicals (i.e., the initiation step).

Unfortunately, when radiation curable compositions are used for food packaging, toys or dental applications, the amount of photoinitiators and related degradation products that are able to diffuse out of the cured coating into the surrounding medium (migration) it's a critical issue. Low molecular weight compounds are usually not completely built into the polymer network and are prone to be extracted or to diffuse out of the cured composition. Therefore, there is a continuous effort in designing photoinitiators having a reduced tendency to migrate out or to be extracted from the cured composition.

One approach to overcome these problems is to use photoinitiators which contain an ethylenically unsaturated moiety, for examples WO 2006/056541, WO 2004/103580 and AU 200/3205731 describe derivatives of acylphosphine oxides with a (meth)acrylated functionality. The ethylenically unsaturated group enables the photoinitiator to be incorporated into the polymeric structure during the curing process.

An alternative approach is to use photoinitiators of increased molecular size, which have an increased probability to be blocked into the cured products, resulting in reduced levels of migratable and/or extractable products. This solution is disclosed in U.S. Pat. No. 6,296,986, U.S. Pat. No. 7,354,957, U.S. Pat. No. 7,166,647, EP 1616921 and EP 1674499. It is also possible to combine the advantages of greater molecular size and ethylenic unsaturation in the same compound as disclosed in US 2012/0046376.

However, the expert in the art knows that both kind of photoinitiators have a tendency to lose reactivity. Hence, considerable amounts of active substance are often required in order to reach the desired curing speed, thereby also increasing the viscosity to an undesirable level for a great number of applications of radiation curable compositions, such as e.g. ink-jet printing. Unfortunately, above a concentration of 10-12% of non-acrylate functional materials, either start to behave as plasticizers or just reduce the crosslink density of the cured film to a point where its mechanical properties are impaired.

Moreover, the presence of an ethylenically unsaturated group limit the thermal and storage stability of these photoinitiators.

Furthermore, the solubility and compatibility with the photocurable system of certain photoinitiators, such as those with high molecular weight or containing unsaturated groups, can be limited.

That means that there continues to be a demand for other photoinitiators which do not migrate and having improved reactivity and compatibility with radiation-curable systems.

Mono- and bis-acylphosphine oxides are widely used as photoinitiators in radiation curable compositions. They are highly reactive and non-yellowing and have a small absorption band around 350-420 nm which makes them also suitable for LED lamps. All these characteristics make of acylphosphine oxides a unique class of photoinitiators suitable for a wide range of applications. Unfortunately they show the same applicative limits mentioned above.

We have now discovered a series of novel multifunctional mono- and bis-acylphoshine oxide photoinitiators, which do not contain photocurable ethylenically unsaturated groups, with good solubility, high reactivity and stability, and a very low tendency to migrate and/or to be extracted.

These multifunctional mono- and bis-acylphosphine oxides are obtainable as the reaction product of a multifunctional compound containing three or more reactive groups, also defined as core, with a compound containing a mono- or bis-acylphosphine oxide group.

Surprisingly they show a reactivity per phosphor unit superior to the reactivity of the monofunctional acylphosphine oxide photoinitiators. On the contrary the prior art photoinitiators described in WO 2012/0046376, U.S. Pat. No. 7,354,957 and U.S. Pat. No. 7,166,647 have a lower reactivity and must be dosed in higher quantities in the photocurable compositions.

At the same time, the relatively small molecular weight of the core makes the photoinitiators highly soluble in photocurable compositions, especially in photocurable coating compositions.

DESCRIPTION OF THE INVENTION

It is a fundamental object of the present invention photoinitiators of formula I:

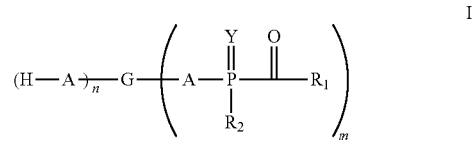

wherein:
each A represents independently of one another O, S, $NR_3$;
G is a residue of the multifunctional compound (core) $G-(A-H)_{m+n}$, wherein each A-H represents a alcoholic or amino or thiol group;
m and n are both integer numbers and m+n is comprised between 3 and 10;
m is comprised between 3 and 8;
$R_1$, $R_2$ are independently of one another, $C_1$-$C_{18}$ alkyl, $C_5$-$C_{12}$ aryl and $C_5$-$C_{12}$ cycloalkyl, each of which is uninterrupted or interrupted by one or more oxygen and/or sulfur atoms and/or one or more substituted or unsubstituted imino groups, or are a five- to six-membered heterocyclic radical containing oxygen and/or nitrogen and/or sulfur atoms, where each of said radicals may be substituted by aryl, alkyl, aryloxy, alkoxy, heteroatoms and/or heterocyclic radicals;

$R_2$ may also be $R_1$—(C=O)—;

Y is O or S;

$R_3$ is hydrogen or $C_1$-$C_4$ alkyl;

with the proviso that the photoinitiators of formula I do not contain photocurable ethylenically unsaturated groups.

It is another object of the present invention a photocurable composition comprising:
 a) from 0.05 to 20% by weight (% wt), preferably from 0.2 to 10% by weight, of at least one photoinitiator of formula I;
 b) from 30 to 99.9% by weight, preferably from 50 to 98.9 by weight, of at least one ethylenically unsaturated compound.

It is an object of the present invention a process for photocuring the photocurable composition above described, which process comprises the following steps:
 I) providing said photocurable composition;
 II) photocuring the photocurable composition with a light source.

DETAILED DESCRIPTION OF THE INVENTION

Preferably, in formula I m+n is comprised between 3 and 8, and more preferably between 3 and 6.

Preferably in formula I, m is comprised between 3 and 6 and more preferably between 3 and 5.

When n is different from 0, the compounds of formula I have free alcoholic groups and/or amino groups and/or thiol groups.

In an embodiment of the present invention, in formula I, A is only oxygen. In this case $G\text{-}(A\text{-}H)_{m+n}$ is a polyhydroxy compound, which can be selected from monomeric, oligomeric and, polymeric polyols, and mixture thereof.

Examples of suitable monomeric and oligomeric polyols are glycerol, di-glycerol, tri-glycerol, triethanolamine, trimethylol propane, di-trimethylol propane, pentaerythritol, di-pentaeritrithol, sugar alcohols, such as sorbitol, mannitol and xylitol, mixtures thereof.

Examples of polymeric polyols are alkoxylated compounds, polyhydroxy polyethers, which can be both aliphatic or aromatic, polyhydroxy polyesters, polyhydroxy polyamides, polyhydroxy polyimides, polyhydroxy polycarbonates; styrene-allyl alcohols copolymers.

The alkoxylated compounds are particularly preferred for the realization of the present invention. Examples of such alkoxylated compounds are monomeric and oligomeric polyols mentioned above, which have been alkoxylated, for example ethoxylated and/or propoxylated and/or butoxylated. Other suitable examples are the linear or branched polyamines described below, which have been alkoxylated, and polyalkoxylated diamines, such as ethoxylated ethylene diamine and ethoxylated 1,3-propylene diamine. In the alkoxylated compounds of the invention, each group reactive toward the alkylene oxide can bring from 0 to 15 alkoxy units, preferably from 1 to 6 alkoxy units.

In a preferred embodiment $G\text{-}(A\text{-}H)_{m+n}$ is chosen among monomeric and oligomeric polyols.

In another preferred embodiment $G\text{-}(A\text{-}H)_{m+n}$ is chosen among monomeric and oligomeric polyols which have been ethoxylated and/or propoxylated. According to another embodiment of the present invention, in formula I A is only sulfur. In this case $G\text{-}(A\text{-}H)_{m+n}$ is a polythiol compound, which can be obtained, for instance, by the esterification reaction of a mercapto organic acid with a polyol such as, for example, trimethylolpropane tris-(thioglycolate), pentaerythritol tetrakis-(thioglycolate), trimethylol propane tris-(β-thiopropionate), pentaerythritol tetrakis-(β-thiopropionate), dipentaerythritol poly(β-thiopropionate), etc. The term polythiol compound also include terminal thiol group-containing polyethers, terminal thiol group-containing polythioethers, thiol compounds obtained by a reaction of a polyepoxy compound with hydrogen sulfide; and thiol compounds containing terminal thiol groups which are obtained by a reaction of a polythiol compound with an epoxy compound.

According to a further embodiment of the present invention, in formula I, A is only nitrogen, so that $G\text{-}(A\text{-}H)_{m+n}$ is a linear or branched polyamine. The polyamine may be chosen, for example, from polyethyleneimines, polyvinylamines, polyamine substituted polyalkylene glycols, polyamine substituted poly(meth)acrylate, amine substituted polyesters, polyamino acids, amodimethicones, polyalkyleneamines, such as polyethylenammine, and mixtures thereof. Specific examples are diethylenetriamine, triethylenetetramine, tetraethylenepentamine, spermidine, spermine, 4-aminomethyl-1,8-octanediamine, N-(2-aminoethyl)-1,3-propanediamine, and N,N'-bis(3-aminopropyl) ethylenediamine.

In formula I, A can be a mix of oxygen and/or nitrogen and/or sulfur. In this case $G\text{-}(A\text{-}H)_{m+n}$ can be also a compound which contains different functional groups, for example amino groups and hydroxyl groups. Examples of these compounds are diethanolamine and tris(hydroxymethyl) aminomethane.

Preferably, $G\text{-}(A\text{-}H)_{m+n}$ has a number average molecular weight not greater than 1500, more preferably not greater than 800, and most preferably not greater than 500.

Preferably, $G\text{-}(A\text{-}H)_{m+n}$ is chosen among glycerol, ethoxylated and/or propoxylated glycerol, di-glycerol, ethoxylated and/or propoxylated di-glycerol, trimethylolpropane, ethoxylated and/or propoxylated trimethylolpropane, di-trimethylolpropane, ethoxylated and/or propoxylated di-trimethylolpropane, penthaerythritol, ethoxylated and/or propoxylated penthaerythritol, di-penthaerythritol, ethoxylated and/or propoxylated di-penthaerythritol, sorbitol, ethoxylated and/or propoxylated sorbitol.

Other preferred $G\text{-}(A\text{-}H)_{m+n}$ are triethanolamine, ethoxylated and/or propoxylated triethanolamine, 4-aminomethyl-1,8-octanediamine, N-(2-Aminoethyl)-1,3-propanediamine, tris(hydroxymethyl) aminomethane, diethanolamine, ethoxylated and/or propoxylated diethanolamine, 1-thioglycerol, N,N'-bis(3-aminopropyl) ethylenediamine.

The residue G suitable for the realization of the present invention does not contain photocurable ethylenically unsaturated groups.

In Formula 1 of the present disclosure:

$C_1$-$C_{18}$ alkyl which can be unsubstituted or substituted by aryl, alkyl, aryloxy, alkoxy, heteroatoms and/or heterocyclic radicals, is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl, octadecyl, 1,1-dimethylpropyl, 1,1-dimethylbutyl, 1,1,3,3-tetramethylbutyl, benzyl, 1-phenylethyl, 2-phenyl-ethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-hydroxyethyl, 2-hydroxypropyl, 3-hydroxypropyl, 4-hydroxybutyl, 6-hydroxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, 2-methoxycarbonylethyl, 2-ethoxycarbonylethyl, 2-butoxycarbonylpropyl, 1,2-di(methoxycarbonyl) ethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, butylthiomethyl, 2-dodecylthioethyl, 2-phenylthioethyl, 2,2,2-trifluoroethyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl;

$C_6$-$C_{12}$ aryl, which is unsubstituted or substituted by aryl, alkyl, aryloxy, alkoxy, heteroatoms and/or heterocyclic radicals is, for example, phenyl, tolyl, xylyl, 4-biphenylyl, 2-, 3- or 4-chlorophenyl, 2,6- or 2,4-dichlorophenyl, 2,4,6-trichlorophenyl, 2-, 3- or 4-fluorophenyl, 2,6- or 2,4-fluorophenyl, 2,4,6-trifluorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, dodecylphenyl, 2-, 3- or 4-methoxyphenyl, 2,6- or 2,4-dimethoxyphenyl, 2-, 3- or 4-ethoxyphenyl, 2,6- or 2,4-diethoxyphenyl, hexyloxyphenyl, α-naphthyl, β-naphthyl, methylnaphthyl, isopropylnaphthyl, chloronaphthyl, ethoxynaphthyl, 2,6-dimethyphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl and ethoxymethylphenyl;

$C_5$-$C_{12}$ cycloalkyl which is unsubstituted or substituted by aryl, alkyl, aryloxy, alkoxy, heteroatoms and/or heterocyclic radicals is, for example, cyclopentyl, cyclohexyl, cyclooctyl, cyclododecyl, methylcyclopentyl, 2,5-dimethylcyclopentyl, methylcyclohexyl, 2,6-dimethylcyclohexyl, 2,6-diethylcyclohexyl, butylcyclohexyl, methoxycyclohexyl, 2,6-dimethoxycyclohexyl, 2,6-diethoxycyclohexyl, butylthiocyclohexyl, chlorocyclohexyl, 2,6-dichlorocyclohexyl, 2,5-dichlorocyclopentyl, and a saturated or unsaturated bicyclic system, for example norbornyl or norbornenyl, a tricyclic system, such as for example adamantyl, a five- to six-membered, oxygen and/or nitrogen and/or sulfur atom-containing heterocyclic radical is, for example, furyl, thiophenyl, pyrryl, pyridyl, indolyl, benzoxazolyl, dioxolyl, dioxyl, benzimidazolyl, benzothiazolyl, dimethylpyridyl, methyiquinolyl, dimethylpyrryl, methoxyfuryl, dimethoxypyridyl, difluoropyridyl, methylthiophenyl, isopropylthiophenyl and tert-butylthiophenyl.

Preferably, $R_1$ is phenyl, tolyl, xylyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, α-naphthyl, β-naphthyl, methylnaphthyl, 4-bromophenyl, 2- or 4-nitrophenyl, 2,4- or 2,6-dinitrophenyl, 4-dimethylaminophenyl, 4-acetylphenyl, cyclopentyl, cyclohexyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, adamantyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, 2- or 3-furyl, 2- or 3-thiophenyl, 2- or 3-pyrryl and dimethylpyrryl.

More preferably, $R_1$ is phenyl, 2,6-dichlorophenyl, 2,4,6-trichlorophenyl, 2,6-dimethylphenyl, 2,4,6-trimethylphenyl, 2,6-diethylphenyl, 2,6-dimethoxyphenyl, 2,6-diethoxyphenyl, α-naphthyl, 2,6-dinitrophenyl, 2,6-dimethylcyclohexyl, 2,6-diethylcyclohexyl, 2,6-dimethoxycyclohexyl, 2,6-diethoxycyclohexyl or 2,6-dichlorocyclohexyl, tert-butyl, pentyl, hexyl, heptyl, octyl and 2-ethylhexyl.

Most preferably, $R_1$ is phenyl, 2,6-dichlorophenyl, 2,4,6-trichlorophenyl, 2,6-dimethylphenyl, 2,4,6-trimethylphenyl, 2,6-dimethoxyphenyl and tert-butyl.

Preferably, $R_2$ is $R_1$—(C=O)—, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, benzyl, p-chlorobenzyl, 2,4-dichlorobenzyl, p-methoxybenzyl, phenyl, tolyl, xylyl, 4-biphenylyl, 2-, 3- or 4-chlorophenyl, 2,4- or 2,6-dichlorophenyl, 2,4,6-trichlorophenyl, 2-, 3- or 4-methylphenyl, 2,4- or 2,6-dimethylphenyl, 2,4,6-trimethylphenyl, 2-, 3- or 4-ethylphenyl, 2,4- or 2,6-diethylphenyl, 2-, 3- or 4-iso-propylphenyl, 2-, 3- or 4-tert-butylphenyl, 2-, 3- or 4-methoxyphenyl, 2,4- or 2,6-dimethoxyphenyl, 2-, 3- or 4-ethoxyphenyl, α-naphthyl, methylnaphthyl, chloronaphthyl, ethoxynaphthyl, 2- or 4-nitrophenyl, 2,4- or 2,6-dinitrophenyl, 4-dimethylaminophenyl and 4-acetylphenyl.

More preferably, $R_2$ is $R_1$—(C=O)—, methyl, ethyl, propyl, isopropyl, n-butyl, sec-butyl, tert-butyl, pentyl, hexyl, 2-ethylhexyl, phenyl, xylyl, 4-biphenylyl, 2-, 3- or 4-chlorophenyl, 2,4-dichlorophenyl, 2-, 3- or 4-methylphenyl, 2,4-dimethylphenyl, 2-, 3- or 4-ethylphenyl, 2-, 3- or 4-methoxyphenyl, 2,4-dimethoxyphenyl, 2-, 3- or 4-ethoxyphenyl, α-naphthyl, methylnaphthyl, chloronaphthyl, ethoxynaphthyl and 2- or 4-nitrophenyl.

Most preferably, $R_2$ is $R_1$—(C=O)—, methyl, ethyl, propyl, isopropyl, n-butyl, sec-butyl, tert-butyl, phenyl, 4-biphenylyl, 2-, 3- or 4-chlorophenyl, 2-, 3- or 4-methylphenyl, 2-, 3- or 4-methoxyphenyl or 2-, 3- and 4-ethoxyphenyl.

Again, $R_1$ and $R_2$ suitable for the realization of the present invention do not contain photocurable ethylenically unsaturated groups.

Y is preferably O.

$R_3$ is hydrogen or $C_1$-$C_4$ alkyl, which is, for example, methyl, ethyl, propyl, isopropyl, n-butyl, sec-butyl and tert-butyl.

In a particularly preferred embodiment $R_1$ is 2,4,6-trimethylphenyl and $R_2$ is phenyl.

Typical multifunctional mono- and bis-acylphosphine oxides according to formula I are described in Table 1, without being limited there to. In case of a polymeric multifunctional core it is obvious for those skilled in the art that the described multifunctional acylphosphine oxide photoinitiators have a distribution in molecular weight. In the structures, a, b, c, d, e and f are integer and they are independently comprised between 0 and 15.

TABLE 1
PI-1
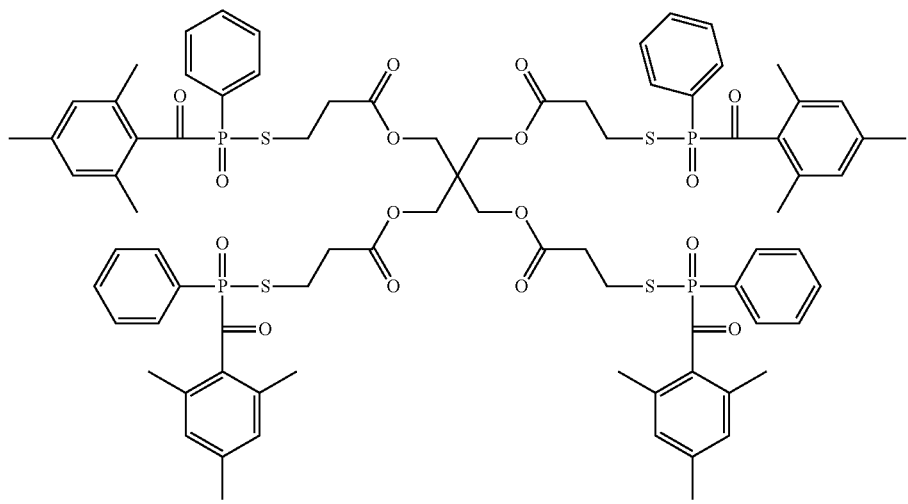
PI-2
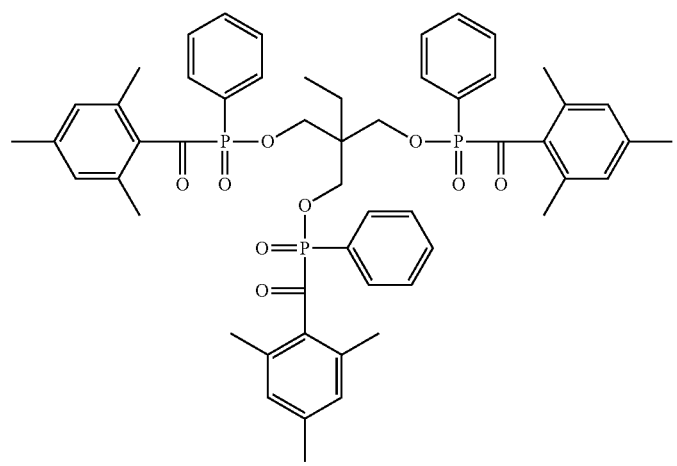
PI-3
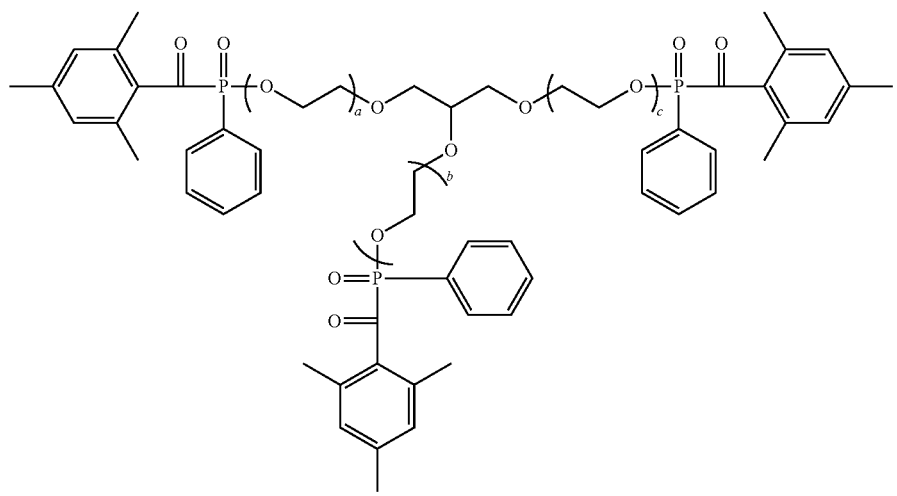

TABLE 1-continued
PI-4
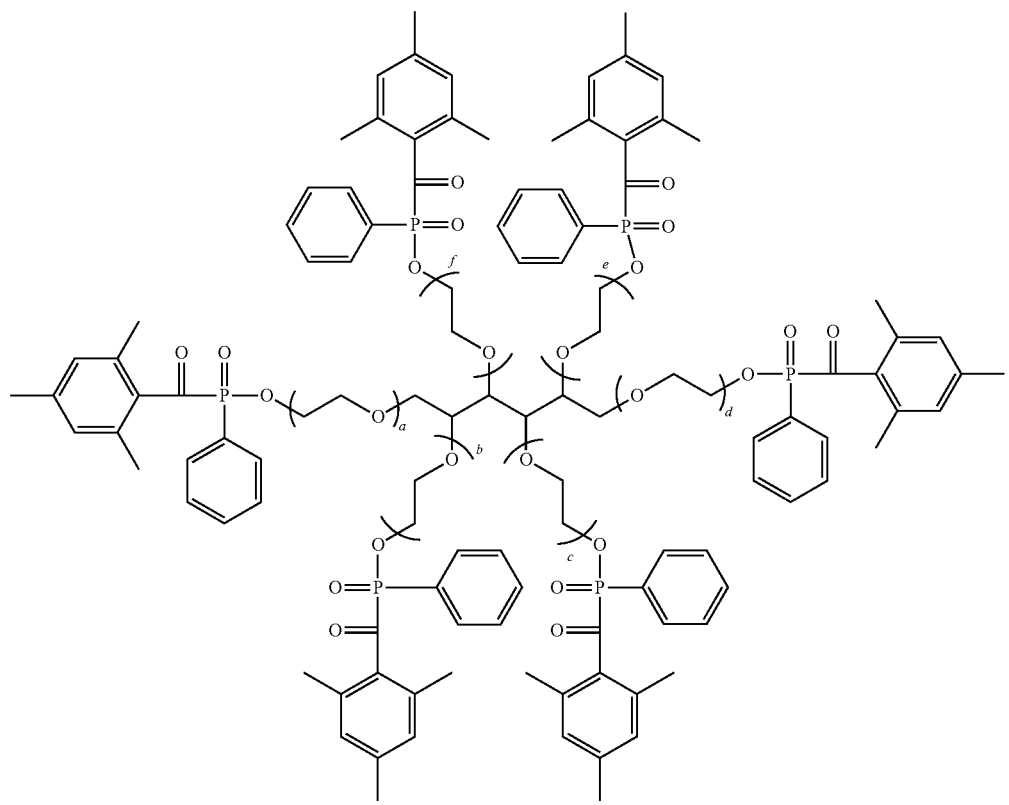
PI-5
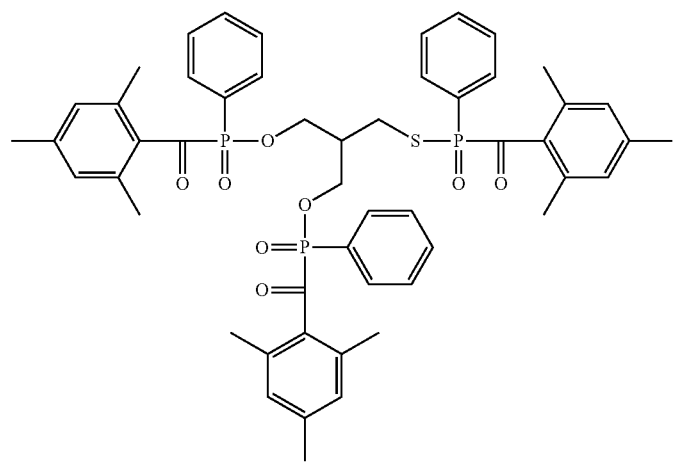
PI-6
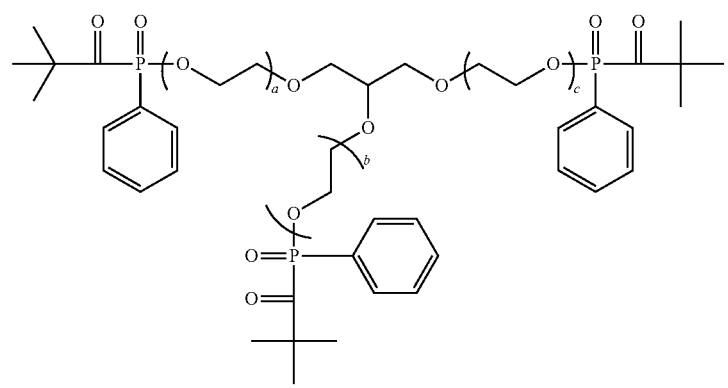

TABLE 1-continued
PI-7
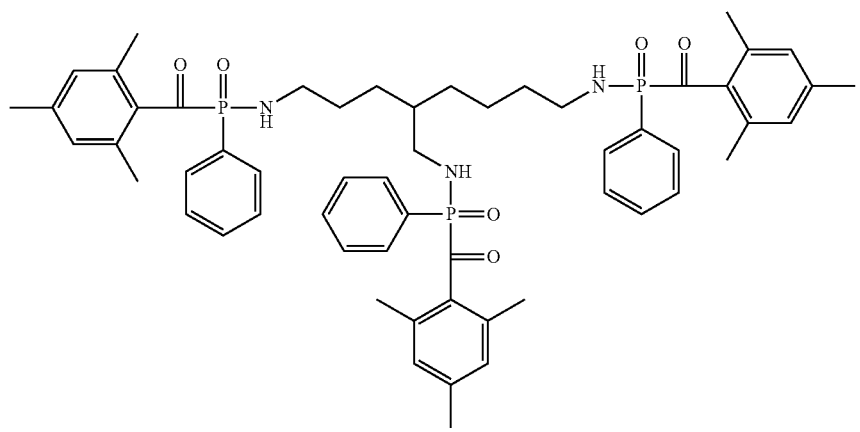
PI-8
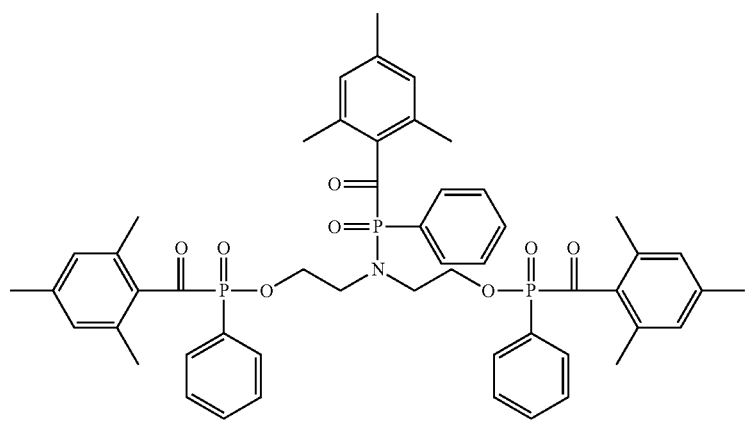
PI-9
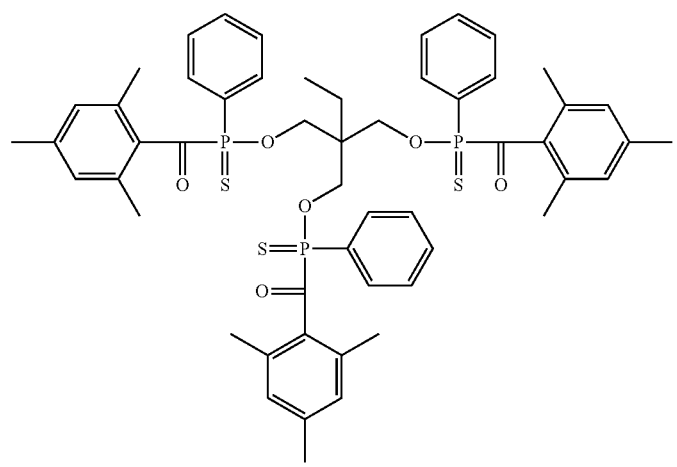

TABLE 1-continued
PI-10
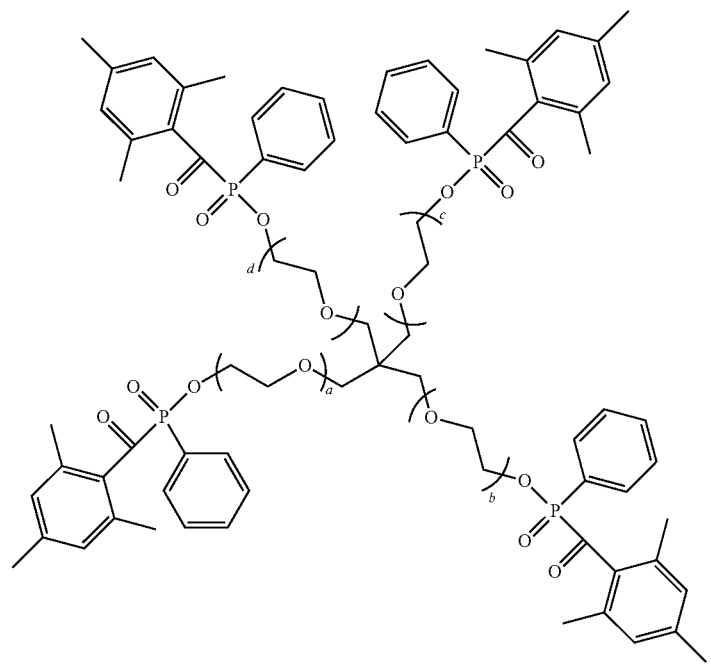
PI-11
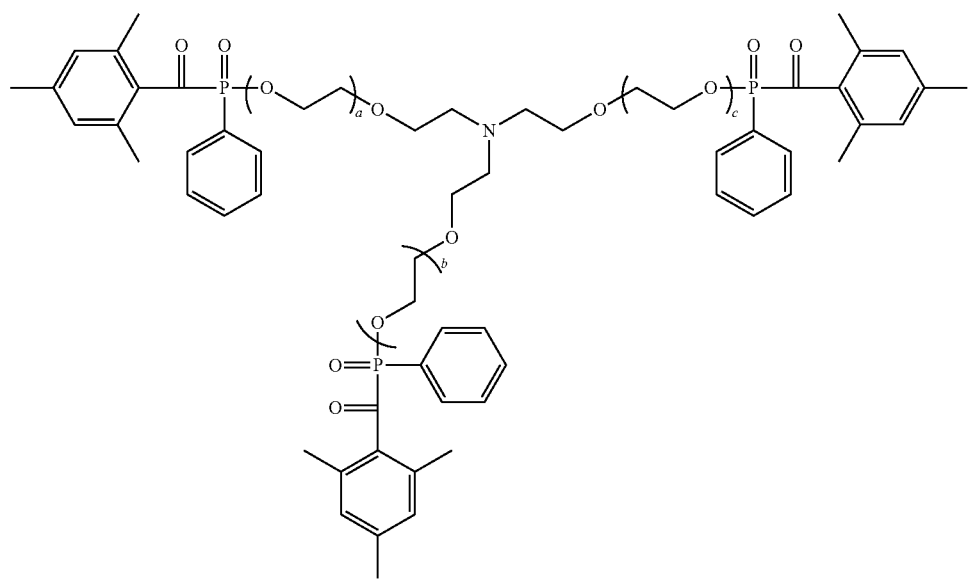

TABLE 1-continued
PI-12
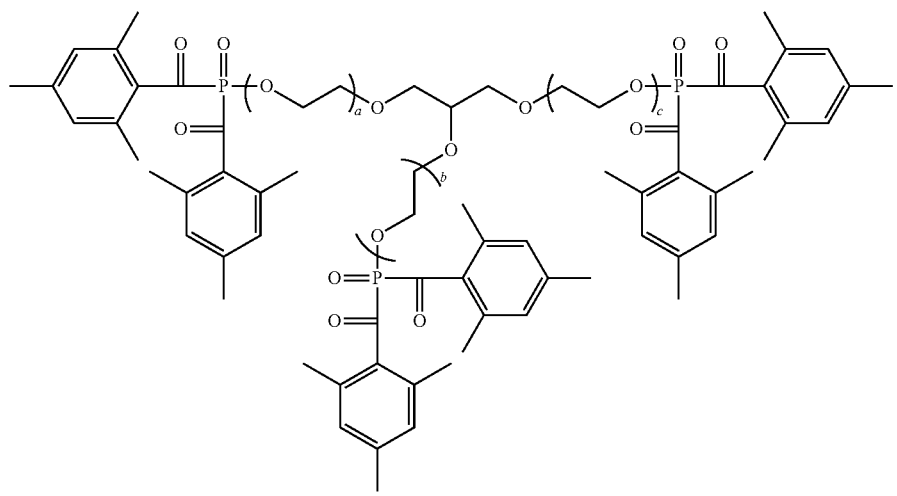
PI-13
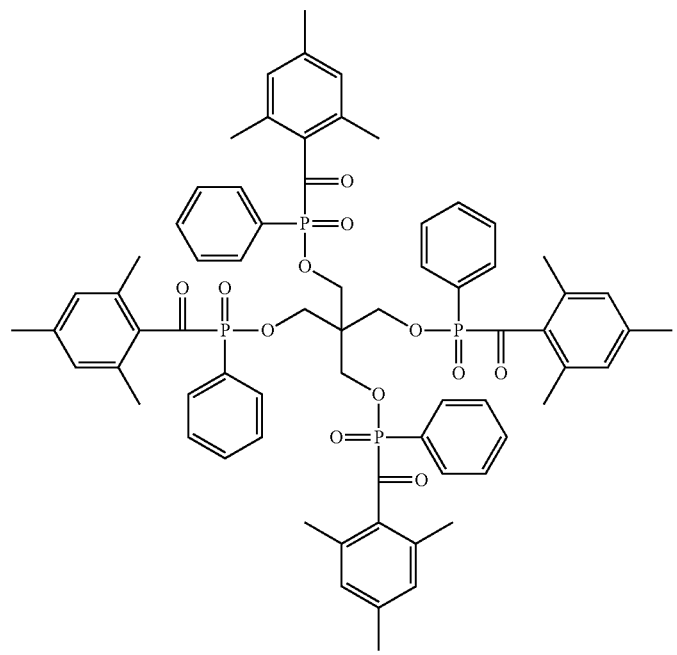

TABLE 1-continued
PI-14
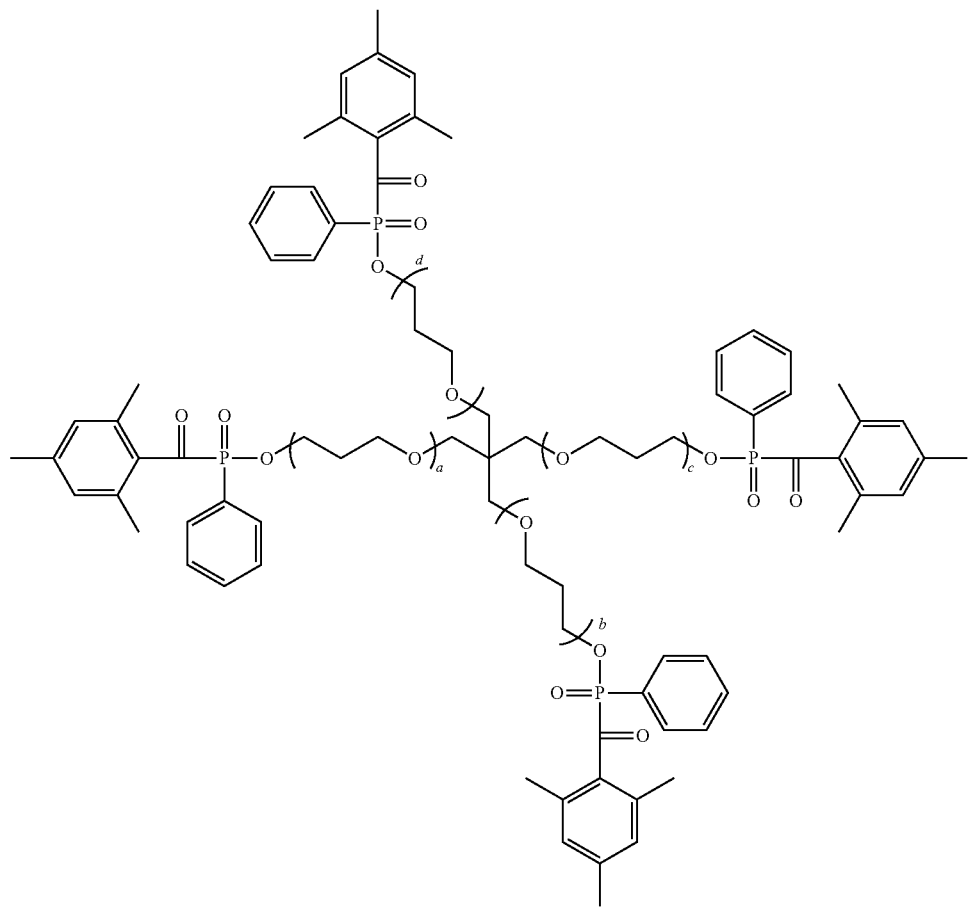
PI-15
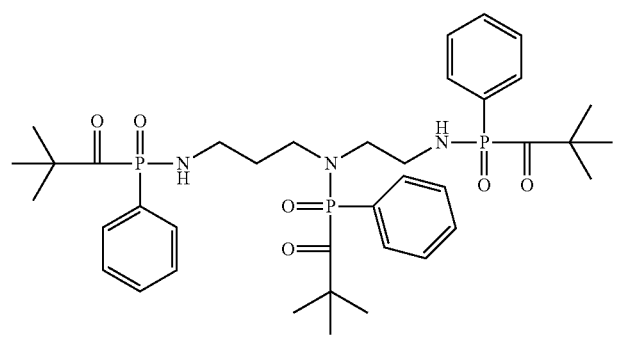 [SMILES: CC(C)(C)C(=O)P(=O)(NCCCN(CCNP(=O)(C(=O)C(C)(C)C)c1ccccc1)P(=O)(C(=O)C(C)(C)C)c1ccccc1)c1ccccc1]

TABLE 1-continued

PI-16

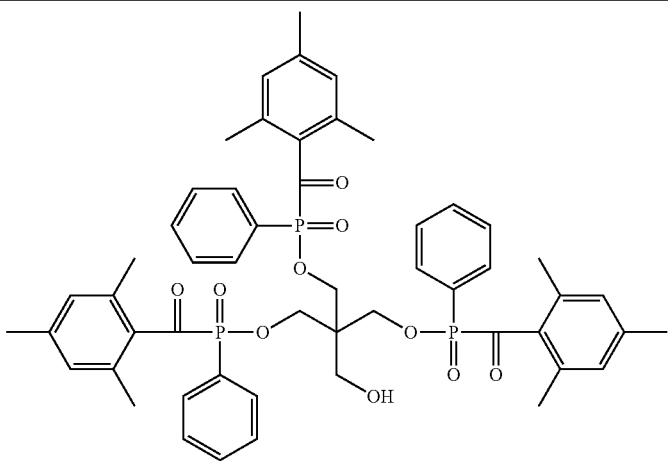

PI-17

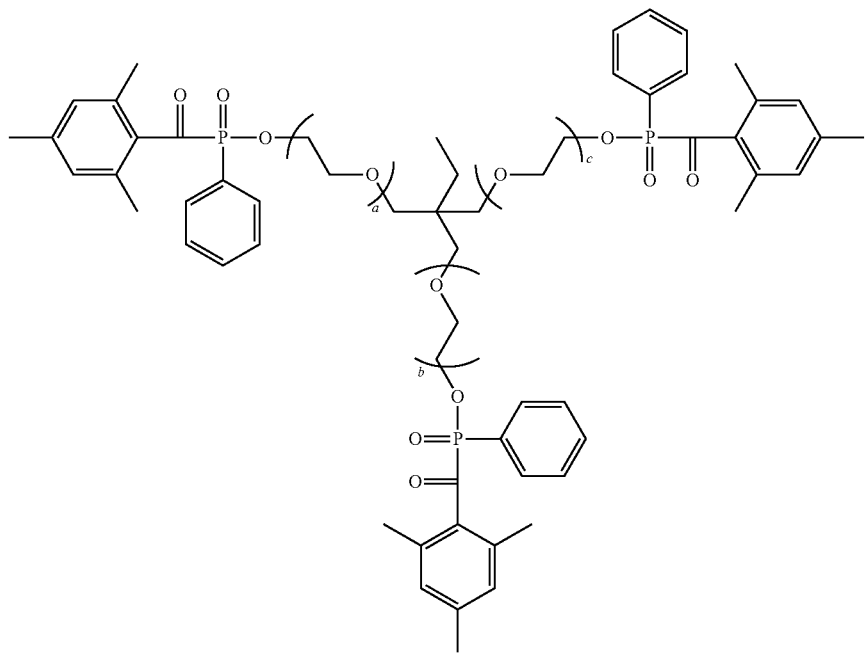

The compounds of formula I can be prepared according conventional method known to the expert in the art, for example according to the following process:

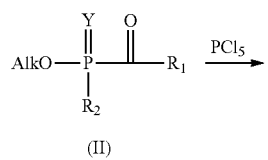
(II)

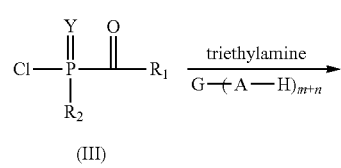
(III)

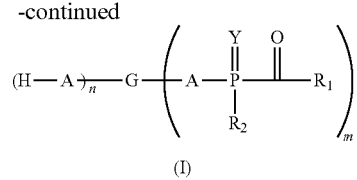
(I)

In particular, the phosphinic chloride of formula III can be synthesized by reaction of the corresponding alkylester with PCl$_5$ (as described in Methoden der Organischen Chemie, Vol. 12/1 p. 241). Then, the phosphinic chloride of formula HI can react with G-(A-H)$_{m+n}$ in the presence of triethylamine to give said products of formula I.

Accordingly, the compound of formula III can react with G-(A-H)$_{m+n}$ giving an ester (reaction of phosphinic chloride with an alcohol), a thioester (reaction of phosphinic chloride with a thiol) or an amide (reaction of phosphinic chloride with an amine) of formula I.

A further method of obtaining compound of formula III is described in DE 10206117, wherein the corresponding phosphinic acid (IV) is transformed in the phosphinic chloride (III) by thionyl chloride in the presence of pyridine.

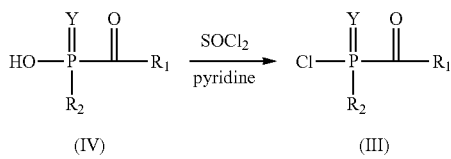

Another method of obtaining compound of formula I is described in Methoden der Organischen Chemie, Vol. 12/1 p. 500, where the alkylester of formula H is directly transformed in compound of formula I by transesterification with G-(A-H)$_{m+n}$ in the presence of sodium.

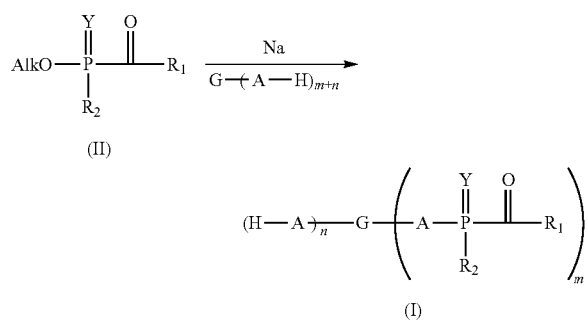

According to the invention, the photoinitiators of formula I can be used to prepare photocurable compositions comprising ethylenically unsaturated compounds b).

The unsaturated compounds b) can contain one or more olefinic double bonds. They can have low-molecular weight (monomeric) or high-molecular weight (oligomeric).

Examples of suitable low molecular weight monomers having one double bond are alkyl or hydroxyalkyl acrylates or methacrylates, such as methyl, ethyl, butyl, 2-ethylhexyl or 2-hydroxyethyl acrylate, isobornyl acrylate and methyl or ethyl methacrylate. Also of interest are resins modified with silicon or fluorine, e.g. silicone acrylates. Further examples of these monomers are acrylonitrile, acrylamide, methacrylamide, N-substituted (meth)acrylamides, styrene, alkylstyrenes and halogeno styrenes, vinyl esters such as vinyl acetate, vinyl ethers such as iso-butyl vinyl ether, N-vinylpyrrolidone, vinyl chloride or vinylidene chloride.

Examples of monomers having more than one double bond are the ethylene glycol diacrylate, propylene glycol diacrylate, neopentyl glycol diacrylate, hexamethylene glycol diacrylate, bisphenol A diacrylate, 4,4'-bis-(2-acryloyloxyethoxy)-diphenylpropane, trimethylolpropane triacrylate, pentaerythritol triacrylate or tetraacrylate, vinyl acrylate, divinyl benzene, divinyl succinate, diallyl phthalate, triallyl phosphate, triallyl isocyanurate or tris-(2-acryloylethyl) isocyanurate.

Examples of high-molecular weight (oligomeric) polyunsaturated compounds are acrylated epoxy resins, acrylated or vinyl-ether- or epoxy-group-containing polyesters, acrylated polyurethanes or acrylated polyethers. Further examples of unsaturated oligomers are unsaturated polyester resins which are usually prepared from maleic acid, phthalic acid and one or more diols and which have molecular weights of from about 500 to 3000. Such unsaturated oligomers can also be described as prepolymers.

Examples of compounds, which are particularly suitable for the realization of the present invention, are esters of ethylenically unsaturated carboxylic acids and polyols or polyepoxides, and polymers containing ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, as well as mixtures of one or more than one such polymers.

Illustrative examples of unsaturated carboxylic acids or anhydrides, useful for the preparation of said esters, are acrylic acid, methacrylic acid, maleic anhydride, crotonic acid, itaconic acid, cinnamic acid and unsaturated fatty acids such as linolenic acid and oleic acid. Acrylic and methacrylic acid are preferred.

Polyols which can be esterified are aromatic and aliphatic and cycloaliphatic polyols, preferably aliphatic and cycloaliphatic polyols.

Aromatic polyols are, for example, hydroquinone, 4,4'-dihydroxydiphenyl, 2,2-di(4-hydroxyphenyl) propane, as well as novolacs and resoles.

Examples of aliphatic and cycloaliphatic polyols include alkylenediols containing preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethyl cyclohexane, glycerol, tris (β-hydroxy-ethyl)amine, trimethylolethane, trimethylolpropane, pentaerythritol, di-pentaerythritol and sorbitol.

Polyepoxides, which can be esterified, include those based on the said polyols, especially the aromatic polyols and epichlorohydrin. Also suitable as polyols are polymers and copolymers that contain hydroxyl groups in the polymer chain or in side groups, for example polyvinyl alcohol and copolymers thereof or poly(meth)acrylic acid hydroxyalkyl esters or copolymers thereof. Further suitable polyols are oligoesters carrying hydroxyl terminal groups.

Further suitable ethylenically unsaturated compounds b) are unsaturated polyamides obtained from unsaturated carboxylic acids and aromatic, aliphatic and cycloaliphatic polyamines having preferably from 2 to 6, more preferably from 2 to 4, amino groups. Examples of such polyamines are: ethylenediamine, 1,2- or 1,3-propylenediamine, 1,2-, 1,3- or 1,4-butylenediamine, 1,5-pentylenediamine, 1,6-hexylenediamine, octylenediamine, dodecylene diamine, 1,4-diaminocyclohexane, isophoronediamine, phenylene diamine, bisphenylenediamine, di-(β-aminoethyl) ether, diethylene triamine, triethylenetetramine and di(β-aminoethoxy)- and di(β-aminopropoxy)ethane. Other suitable polyamines are polymers and copolymers which may contain additional amino groups in the side chain and oligoamides containing amino end groups.

Specific examples of such unsaturated polyamides are: methylenebisacrylamide, 1,6-hexa methylene bisacrylamide, diethylenetriamine trismethacrylamide, bis(methacrylamidopropoxy) ethane and N-[(β-hydroxyethoxy)ethyl]-acrylamide.

Unsaturated polyurethanes are also suitable for the realization of the present invention, for example those derived from saturated or unsaturated diisocyanates and unsaturated or saturated diols. Polybutadiene and polyisoprene and copolymers thereof are also useful. Suitable comonomers include, for example, olefins, such as ethylene, propene, butene and hexene, (meth)acrylates, acrylonitrile, styrene and vinyl chloride.

Polymers having unsaturated (meth)acrylate groups in the side chain can be used as component b). They may typically be reaction products of epoxy resins based on novolak with (meth)acrylic acid; homo- or copolymers of vinyl alcohol or hydroxyalkyl derivatives thereof that have been esterified with (meth)acrylic acid; and homo- and co-polymers of (meth)acrylates that have been esterified with hydroxyalkyl (meth)acrylates.

The photocurable composition of the present invention can also comprise other photoinitiators c) and/or additives d), in addition to components a) and b).

The other photoinitiators c) can be present in an amount comprised between 0.5 and 15% by weight, preferably between 1 and 10% by weight of the composition.

Examples of suitable other photoinitiators c) are camphorquinone, benzophenone, benzophenone derivatives, acetophenone, acetophenone derivatives, dialkoxyacetophenones, α-hydroxyketones, α-aminoketones, 4-aroyl-1,3-dioxolanes, benzoin alkyl ethers and benzil ketals, e.g. benzil dimethyl ketal, ketosulfones, e.g 1-[4-[(4-benzoyl-phenyl)-thio]-phenyl]-2-methyl-2-[(4-methyl-phenyl)-sulfonyl]-propan-1-one (Esacure 1001, from Lamberti S.p.A.), phenylglyoxylates and derivatives thereof, dimeric phenyl glyoxylates, peresters, e.g. benzophenonetetracarboxylic acid peresters, for example as described in EP 126541, acylphosphine oxide photoinitiators (which can be chosen among mono-acylphosphine oxides, bis-acylphosphine oxides, tris-acylphosphine oxides), halomethyltriazines, hexaaryl bisimidazole/coinitiator systems, e.g. ortho-chlorohexaphenylbisimidazole in combination with 2-mercaptobenzothiazole; ferrocenium compounds or titanocenes, for example dicyclopentadienyl-bis(2,6-difluoro-3-pyrrolophenyl)titanium; O-acyloxime ester photoinitiators.

Examples of α-hydroxyketones and α-aminoketones are 1-hydroxy cyclohexylphenyl ketone, 2-hydroxy-2-methyl-1-phenyl-propane-1-one, 1-[4-(2-hydroxyethoxy)phenyl]-2-hydroxy-2-methyl-1-propane-1-one, 2-hydroxy-1-{4-[4-(2-hydroxy-2-methyl-propionyl)-benzyl]phenyl}-2-methyl-propane-1-one, 2-hydroxy-1-{4-[4-(2-hydroxy-2-methyl-propionyl)-phenoxy]-phenyl}-2-methyl-propan-1-one, 2-methyl-1-(4-methylthiophenyl)-2-morpholinopropane-1-one), 2-benzyl-2-dimethylamino-1-(4-morpholinophenyl)-butane-1-one, and (2-(dimethylamino)-2-[(4-methylphenyl) methyl]-1-[4-(4-morpholinyl) phenyl]-1-butanone).

Examples of O-acyloxime ester photoinitiators are 1,2-octanedione,1-[4-(phenylthio)phenyl]-2-(O-benzoyloxime), ethanone 1-[9-ethyl-6-(2-methylbenzoyl)-9H-carbazole-3-yl] 1-(O-acetyloxime) or those described in GB 2339571.

Examples of acylphosphine oxide photoinitiators include, but are not limited to, bis(2,4,6-trimethylbenzoyl)phenylphosphine oxide, bis(2,6-dimethoxybenzoyl)-2,4,4-trimethylpentyl phosphine oxide, bis(2,4,6-trimethylbenzoyl)-(2,4-dipentyloxyphenyl), 2,4,6-trimethylbenzoyl-diphenyl phosphine oxide and ethyl (2,4,6-trimethylbenzoyl) phenylphosphinate.

Examples of the halomethyltriazines based photoinitiators are 2-[2-(4-methoxy-phenyl)-vinyl]-4,6-bis-trichloromethyl [1,3,5]triazine, 2-(4-methoxy-phenyl)-4,6-bis-trichloromethyl [1,3,5]triazine, 2-(3,4-dimethoxyphenyl)-4,6-bis-trichloromethyl [1,3,5]triazine, 2-methyl-4,6-bis-trichloromethyl [1,3,5] triazine.

Cationic photoinitiators can be also used as additional photoinitiators c), when the photocurable compositions according to the invention are used in hybrid systems (which in this connection mean mixtures of free-radically and cationically curing systems). Examples of suitable cationic photoinitiators are aromatic sulfonium, phosphonium or iodonium salts, as described e.g. in U.S. Pat. No. 4,950,581, or cyclopentadienylarene-iron(II) complex salts, e.g. ($\eta^6$-isopropylbenzene)($\eta^5$-cyclopentadienyl) iron(II) hexafluorophosphate or photolatent acids based on oximes, as described, for example, in GB 2 348 644, U.S. Pat. No. 4,450,598, U.S. Pat. No. 4,136,055, WO 00/10972 and WO 00/26219.

Additives d) can be, for example, photosensitizers, accelerators/co-initiators, thermal initiators, binders, stabilizers, and mixture thereof.

The photocuring process can also be improved by the addition, as further additives (d), of at least a photosensitizer from 0.05 to 12% by weight, preferably from 0.1 to 10% by weight.

Examples of photosensitizers are those commonly used in the art, aromatic carbonyl compounds, e.g. benzophenones, thioxanthones, anthraquinones and 3-acylcoumarin derivatives, terphenyls, styryl ketones, and 3-(aroylmethylene)-thiazolines, camphorquinones and also eosin, rhodamine and erythrosine dyes.

Examples of thioxanthones are thioxanthone, 2-isopropyl thioxanthone, 2-chloro thioxanthone, 2-dodecyl thioxanthone, 2,4-diethyl thioxanthone, 2,4-dimethyl thioxanthone, 1-methoxycarbonyl thioxanthone, 2-ethoxycarbonyl thioxanthone, 3-(2-methoxyethoxycarbonyl) thioxanthone, 4-butoxycarbonyl thioxanthone, 3-butoxycarbonyl-7-methyl thioxanthone, 1-cyano-3-chloro thioxanthone, 1-ethoxycarbonyl-3-chloro thioxanthone, 1-ethoxycarbonyl-3-ethoxy thioxanthone, 1-ethoxycarbonyl-3-amino thioxanthone, 1-ethoxycarbonyl-3-phenylsulfuryl thioxanthone, 3,4-di[2-(2-methoxyethoxy)ethoxycarbonyl] thioxanthone, 1-ethoxycarbonyl-3-(1-methyl-1-morpholinoethyl) thioxanthone, 2-methyl-6-dimethoxymethyl thioxanthone, 2-methyl-6-(1,1-dimethoxybenzyl) thioxanthone, 2-morpholinomethyl thioxanthone, 2-methyl-6-morpholinomethyl thioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxy thioxanthone, 6-ethoxycarbonyl-1-2-methoxythioxanthone, 6-ethoxycarbonyl-2-methylthioxanthone, thioxanthone-2-polyethylene glycol ester, 2-hydroxy-3-(3,4-dimethyl-9-oxo-9H-thioxanthon-2-yloxy)-N,N,N-trimethyl-1-propanaminium chloride, or those described in the patent application PCT/EP2011/069514, such as n-dodecyl-7-methyl-thioxanthone-3-carboxylate and N,N-disobutyl-7-methyl-thioxanthone-3-carbamide. Also suitable are polymeric thioxanthone derivatives (e.g. Omnipol TX from IGM Resins B.V., Genopol TX-1 from Rahn A. G., Speedcure 7010 from Lambson Limited).

Example of benzophenones are benzophenone, 4-phenyl benzophenone, 4-methoxy benzophenone, 4,4'-dimethoxybenzophenone, 4,4'-dimethyl benzophenone, 4,4'-dichloro benzophenone, 4,4'-dimethylamino benzophenone, 4,4'-diethylamino benzophenone, 4-methyl benzophenone, 2,4,6-trimethyl benzophenone, 4-(4-methylthiophenyl) benzophenone, 3,3'-dimethyl-4-methoxy benzophenone, methyl 2-benzoyl benzoate, 4-(2-hydroxyethylthio) benzophenone, 4-(4-tolylthio) benzophenone, 4-benzoyl-N,N,N-trimethylbenzene methanaminium chloride, 2-hydroxy-3-(4-benzoylphenoxy)-N,N,N-trimethyl-1-propanaminium chloride monohydrate, 4-(β-acryloyl-1,4,7,10,13-pentaoxatridecyl) benzophenone, 4-benzoyl-N,N-dimethyl-N-[2-(1-oxo-2-propenyl)oxylethyl-benzene methanaminium chloride. Also suitable are polymeric benzophenone derivatives (e.g. Omnipol BP, Omnipol 2702 and Omnipol 682 all from IGM Resins B.V., Genopol BP-2 from Rahn A. G. and Speedcure 7005 from Lambson Limited).

Examples of 3-acylcoumarin derivatives are 3-benzoyl coumarin, 3-benzoyl-7-methoxy coumarin, 3-benzoyl-5,7-di(propoxy) coumarin, 3-benzoyl-6,8-dichloro coumarin, 3-benzoyl-6-chloro coumarin, 3,3'-carbonyl-bis[5,7-di (propoxy) coumarin], 3,3'-carbonyl-bis(7-methoxy coumarin), 3,3'-carbonyl-bis(7-diethylamino coumarin), 3-isobutyroyl coumarin, 3-benzoyl-5,7-dimethoxy coumarin, 3-benzoyl-5,7-diethoxy coumarin, 3-benzoyl-5,7-dibutoxy coumarin, 3-benzoyl-5,7-di(methoxyethoxy) coumarin, 3-benzoyl-5,7-di(allyloxy) coumarin, 3-benzoyl-7-dimethylamino coumarin, 3-benzoyl-7-diethylamino coumarin, 3-isobutyroyl-1,7-dimethylamino coumarin, 5,7-dimethoxy-3-(1-naphthoyl) coumarin, 5,7-dimethoxy-3(1-naphthoyl)-coumarin, 3-benzoylbenzo [f]coumarin, 7-diethylamino-3-thienoyl coumarin, 3-(4-cyanobenzoyl)-5,7-dimethoxy coumarin, or those described in ITVA20120041.

Examples of 3-(aroylmethylene) thiazolines are 3-methyl-1,2-benzoylmethylene-β-naphtho thiazoline, 3-methyl-2-benzoylmethylene-benzo thiazoline, 3-ethyl-2-propionylmethylene-β-naphtho thiazoline; Examples of other aromatic carbonyl compounds are acetophenone, 3-methoxyacetophenone, 4-phenylacetophenone, benzil, such as that described in WO 2013/164394, 2-acetylnaphthalene, 2-naphthaldehyde, 9,10-anthraquinone, 9-fluorenone, dibenzosuberone, xanthone, 2,5-bis(4-diethylaminobenzylidene) cyclopentanone, α-(para-dimethylamino benzylidene); ketones, such as 2-(4-dimethylamino-benzylidene)-indan-1-one or 3-(4-dimethylaminophenyl)-1-indan-5-yl-propenone, 3-phenylthiophthalimide, N-methyl-3,5-di(ethylthio) phthalimide.

The photocurable compositions of the invention can also conveniently include accelerators/co-initiators, e.g. alcohols, thiols, thioethers, amines or ethers that have an available hydrogen, bonded to a carbon adjacent to the heteroatom, disulfides and phosphines, as described e.g. in EP 438123 and GB 2180358. Such accelerators/co-initiators are generally present in an amount comprised between 0.2 and 15% by weight, preferably from 0.2 to 8% by weight.

Suitable examples of amine accelerators/co-initiators include, but are not limited to, aliphatic, cycloaliphatic, aromatic, aryl-aliphatic, heterocyclic, oligomeric or polymeric amines. They can be primary, secondary or tertiary amines, for example butyl amine, dibutyl amine, tributyl amine, cyclohexyl amine, benzyldimethyl amine, di-cyclohexyl amine, N-phenyl glycine, triethyl amine, phenyldiethanol amine, triethanolamine, piperidine, piperazine, morpholine, pyridine, quinoline, esters of dimethylamino benzoic acid, Michler's ketone (4,4'-bis-dimethyl aminobenzophenone) and corresponding derivatives.

As the amine accelerators/co-initiators, an amine-modified acrylate compound can be used: examples of such amine-modified acrylate include acrylates modified by reaction with a primary or secondary amine that are described in U.S. Pat. No. 3,844,916, EP 280222, U.S. Pat. No. 5,482,649 or U.S. Pat. No. 5,734,002.

Polymeric amine derivatives are also suitable as co-initiators (e.g. Omnipol ASA from IGM Resins B.V., Genopol AB-2 from Rahn A. G., Speedcure 7040 from Lambson Limited).

The curing process, especially in the case of pigmented compositions (e.g. compositions pigmented with titanium dioxide), may also be assisted by the addition, as additional additive d), of thermal initiator, a compound that forms free radicals when heated, e.g. an azo compound, such as 2,2'-azobis(4-methoxy-2,4-dimethylvaleronitrile), a triazene, diazosulfide, pentazadiene or a peroxy compound, for example a hydroperoxide or peroxycarbonate, e.g. tert-butyl hydroperoxide, as described e.g. in EP 245 639.

Binders may also be added to the photocurable composition. The addition of binders is particularly advantageous when the photocurable compounds are liquid or viscous substances. The amount of binder may be, for example, from 5 to 60% by weight, preferably from 10 to 50% by weight. The choice of binder is made in accordance with the field of use and the properties required therefor, such as developability in aqueous and organic solvent systems, adhesion to substrates and sensitivity to oxygen. Suitable binders are, for example, polymers having a molecular weight of approximately from 5,000 to 2,000,000, preferably from 10,000 to 1,000,000. Illustrative examples are: homo- and copolymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, such as cellulose acetate, cellulose acetate butyrate, methylcellulose, ethylcellulose; polyvinylbutyral, polyvinylformal, cyclised rubber, polyethers such as polyethylene oxide, polypropylene oxide, polytetrahydrofuran; polystyrene, polycarbonates, polyurethanes; chlorinated polyolefins, as e.g. polyvinyl chloride, co-polymers of vinyl chloride/vinylidene chloride, co-polymers of vinylidene chloride with acrylonitrile, methyl methacrylate and vinyl acetate, polyvinyl acetate, co-poly (ethylene/vinyl acetate), polymers such as polycaprolactam and poly(hexamethylene adipamide), polyesters such as poly(ethylene glycol terephthalate) and poly(hexamethylene glycol succinate).

Suitable stabilizers are, for example, thermal inhibitors, such as hydroquinone, hydroquinone derivatives, p-methoxyphenol, β-naphthol or sterically hindered phenols, e.g. 2,6-di(tert-butyl)-p-cresol, which prevent premature polymerization. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N,N-diethylhydroxylamine. For the purpose of excluding atmospheric oxygen during polymerization it is possible to add paraffin or similar wax-like substances which, being insoluble in the polymer, migrate to the surface at the beginning of the polymerization and form a transparent surface layer which prevents air from entering.

It is also possible to add a light stabilizer, such as UV absorbers, e.g. hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS).

The compositions according to the invention may also comprise as further additives d) photoreducible dyes, e.g. a xanthene, benzoxanthene, benzothioxanthene, thiazine, pyronin, porphyrin or acridine dye, and/or radiation cleavable trihalomethyl compounds. These compounds are described, for example, in EP 445624.

Further customary additives d) are, depending upon the intended use, optical brighteners, fillers, pigments, both white and colored pigments, colorants, antistatics, wetting agents, flow improvers and and adhesion enhancers.

It is also possible for chain-transfer reagents customary in the art to be added to the compositions according to the invention. Examples are mercaptans, amines and benzothiazole.

For curing thick and pigmented coatings it is suitable to add glass microbeads or pulverised glass fibers, as described e.g. in U.S. Pat. No. 5,013,768.

The composition of the invention may also comprise colorants and/or white or colored pigments. Depending upon the intended use, both inorganic and organic pigments may be used. Such additives will be known to the person skilled in the art; some examples are titanium dioxide pigments, e.g. of the rutile or anatase type, carbon black, zinc oxide, such as zinc white, iron oxides, such as iron oxide yellow, iron oxide red, chromium yellow, chromium green, nickel-titanium yellow, ultramarine blue, cobalt blue, bismuth vanadate, cadmium yellow and cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketopyrrolo-pyrrole, isoindolinone, e.g. tetrachloroisoindolinone, isoindoline, dioxazine, benzimidazolone and quinophthalone pigments. The pigments may be used in the formulations on their own or in admixture.

Depending upon the intended use, the pigments can be added to the formulations in amounts customary in the art, for example in an amount from 0.1 to 30% by weight or from 10 to 25% by weight, based on the total mass.

The composition may also comprise, for example, organic colorants of an extremely wide variety of classes. Examples are azo dyes, methine dyes, anthraquinone dyes and metal complex dyes. Usual concentrations are, for example, from 0.1 to 20% wt, especially from 1 to 5% wt, based on the total mass.

The choice of additives is governed by the field of use in question and the properties desired for that field. The additives d) described above are customary in the art and are accordingly used in the amounts customary in the art.

The photocurable compositions can be used for various purposes, for example as a printing ink, such as screen printing inks, flexographic printing inks, offset printing inks and inkjet printing inks, as clearcoats, as colored coats, as whitecoats, for example for wood or metal, as powder coatings, as coating materials inter alia for paper, wood, metal or plastics, as daylight-curable paints for marking structures and roads, for photographic reproduction processes, for holographic recording materials, for image-recording processes or in the production of printing plates that can be developed using organic solvents or using aqueous-alkaline media, for the production of masks for screen printing, as dental filling compounds, as adhesives, as pressure-sensitive adhesives, as laminating resins, as photoresists, e.g. galvanoresists, as etch resists or permanent resists, both liquid and dry films, as photostructurable dielectrics, and as solder masks for electronic circuits, as resists in the production of color filters for any type of display screen or in the creation of structures during the manufacture of plasma displays and electroluminescent displays, in the production of optical switches, optical gratings (interference gratings), in the manufacture of three-dimensional articles by bulk curing (UV curing in transparent moulds) or according to the stereolithography process, as described, for example, in U.S. Pat. No. 4,575,330, in the manufacture of composite materials (e.g. styrene polyesters which may include glass fibers and/or other fibers and other adjuvants) and other thick-layered compositions, in the coating or sealing of electronic components or as coatings for optical fibers. The compositions are also suitable for the production of optical lenses, e.g. contact lenses or Fresnel lenses, in the manufacture of medical apparatus, aids or implants, in dry film paints.

The compositions are also suitable for the preparation of gels having thermotropic properties. Such gels are described e.g. in DE 19700064 and EP 678534.

The compounds and compositions according to the invention may also be used as free-radical photoinitiators or photoinitiating systems for radiation-curable powder coatings.

The photocurable compositions according to the invention are suitable, for example, as coating materials for all kinds of substrate, for example wood, textiles, paper, ceramics, glass, plastics, such as polyesters, polyethylene terephthalate, polyolefins and cellulose acetate, especially in the form of films, and also metals, such as Al, Cu, Ni, Fe, Zn, Mg or Co and GaAs, Si or $SiO_2$, to which a protective layer is to be applied or an image is to be applied e.g. by imagewise exposure.

The photocuring process according to the invention is generally performed by exposing the photocurable compositions to light from approximately 200 nm to approximately 600 nm. Accordingly a large number of the most varied kinds of light source may be used. Both point sources and planiform radiators (lamp carpets) are suitable. Examples are: carbon arc lamps, xenon arc lamps, medium pressure, high pressure and low pressure mercury arc radiators, doped, where appropriate, with metal halides (metal halide lamps), microwave-excited metal vapour lamps, excimer lamps, superactinic fluorescent tubes, fluorescent lamps, argon incandescent lamps, flash lamps, photographic floodlight lamps, light-emitting diodes (LED), electron beams, X-rays and lasers. The distance between the lamp and the substrate according to the invention to be exposed may vary according to the intended use and the type and strength of the lamp and may be, for example, from 1 cm to 150 cm.

Examples of preparation of acylphosphine oxides of formula I and photocurable compositions according to the invention, only for illustrative purpose and not limitative, are reported in the following paragraphs.

EXAMPLES

Example 1

Preparation of PI-1:

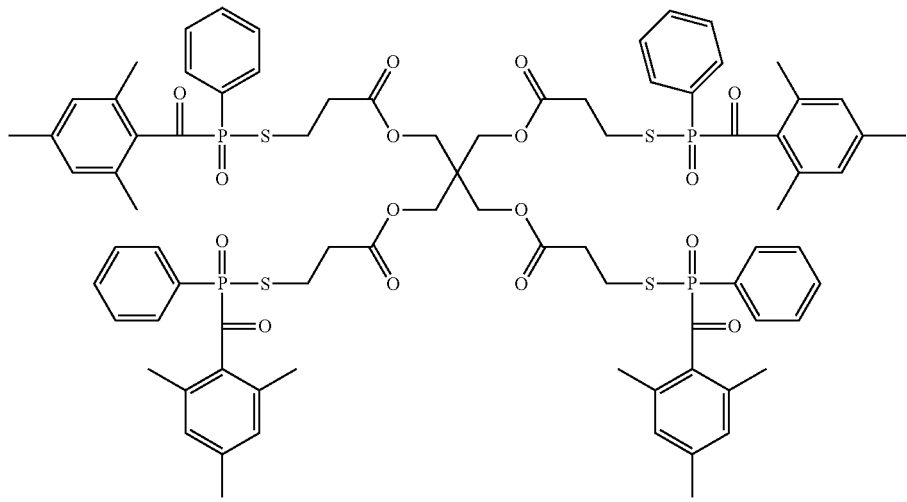

A solution of 20 ml of toluene, 1.41 g of triethylamine and 3.88 g of phenyl(2,4,6-trimethylbenzoyl)phosphinic chloride (prepared according to DE 10206117) was heated to 50° C. under nitrogen atmosphere. 1.28 g of pentaerythritol tetrakis(3-mercaptopropionate) were added and the solution was stirred for one hour. The reaction mixture was cooled to room temperature and 10 ml of deionized water were added. The organic phase was separated, washed once with 20 ml of a saturated water solution of NaHCO$_3$ and twice with 20 ml of water and finally dried over Na$_2$SO$_4$. The solvent was removed under reduced pressure. The reaction product was purified by flash column chromatography on silica gel (toluene/ethyl acetate 8:2) obtaining 2.1 g of photoinitiator, as a viscous liquid.

$^1$H-NMR (CDCl$_3$, δ ppm): 2.10 (s, 24H), 2.24 (s, 12H), 2.64 (t, 8H), 2.91-3.16 (m, 8H), 3.99 (t, 8H), 6.80 (s, 8H), 7.41-7.51 (m, 8H), 7.51-7.61 (m, 4H), 7.81-7.91 (m, 8H)

Example 2

Preparation of PI-3 (Wherein a+b+c is About 8.5):

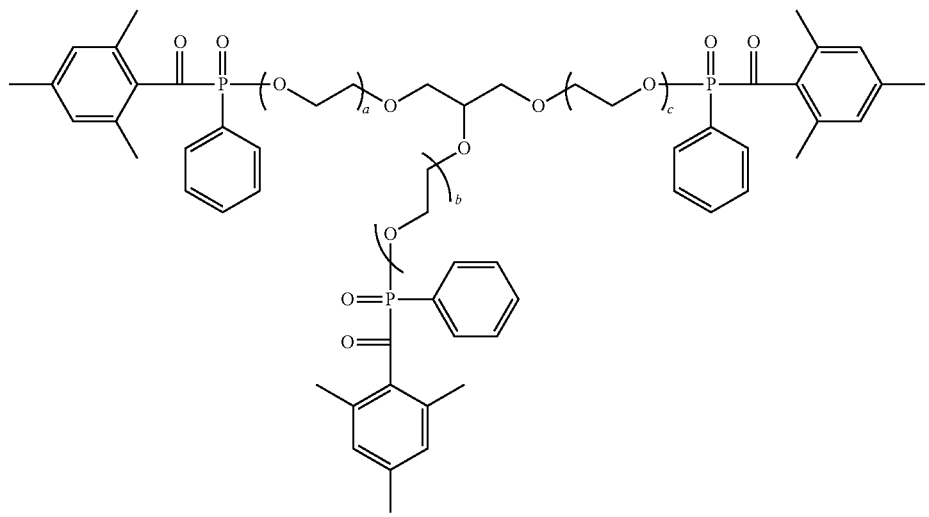

A solution of 150 ml of dichloromethane, 3.49 g of triethylamine and 5.31 g of phenyl(2,4,6-trimethylbenzoyl)phosphinic chloride was heated to 50° C. under nitrogen atmosphere. 1.5 g of Aionico GL/609 (ethoxylathed glycerol, Lamberti S.p.A.) were added and the solution was stirred for 2 hours. The reaction mixture was cooled to room temperature and 10 ml of deionized water were added. The organic phase was separated, washed three times with 100 ml of a saturated water solution of $NaHCO_3$ and twice with 100 ml of water and dried over $Na_2SO_4$. The solvent was removed under reduced pressure obtaining 2.99 g of photoinitiator, as a viscous liquid.

$^1$H-NMR ($CDCl_3$, δ ppm): 2.08 (s, 18H), 2.21 (s, 9H), 3.31-3.78 (m, 34H), 4.03-4.19 (m, 6H), 6.75 (s, 6H), 7.36-7.48 (m, 6H), 7.48-7.58 (m, 3H), 7.71-7.82 (m, 6H)

$^{31}$P-NMR ($CDCl_3$, δ ppm): 18.2

Example 3

Preparation of PI-4 (Wherein a+b+c+d+e+f is About 21):

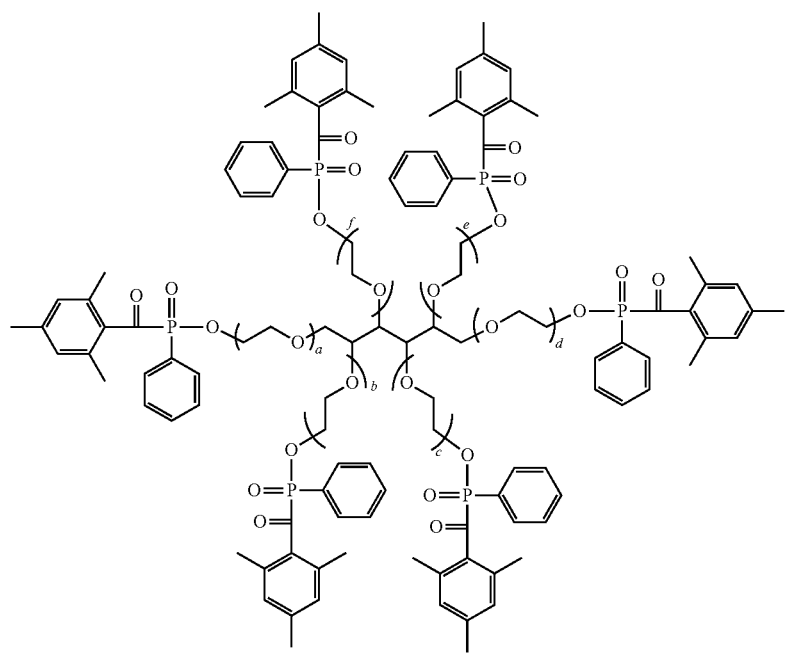

A solution of 70 ml of toluene, 2.44 g of triethylamine and 3.5 g of phenyl(2,4,6-trimethylbenzoyl)phosphinic chloride was heated to 50° C. under nitrogen atmosphere. 3 g of Sorbilene RE/20 (ethoxylathed sorbitol, Lamberti S.p.A.) were added and the solution was stirred for one hour. The reaction mixture was cooled to room temperature and 50 ml of deionized water were added. The organic phase was separated, washed once with 50 ml of a saturated water solution of $NaHCO_3$ and twice with 50 ml of water and finally dried over $Na_2SO_4$. The solvent was removed under reduced pressure obtaining 2.1 g of photoinitiator, as a viscous liquid.

$^1$H-NMR ($CDCl_3$, δ ppm): 2.10 (s, 36H), 2.23 (s, 18H), 3.42-3.91 (m, 100H), 4.04-4.28 (m, 12H), 6.78 (s, 12H), 7.42-7.51 (m, 12H), 7.54-7.62 (m, 6H), 7.74-7.88 (m, 12H)

$^{31}$P-NMR ($CDCl_3$, δ ppm): 18.2

Example 4

Preparation of PI-10 (Wherein a+b+c+d is about 5):

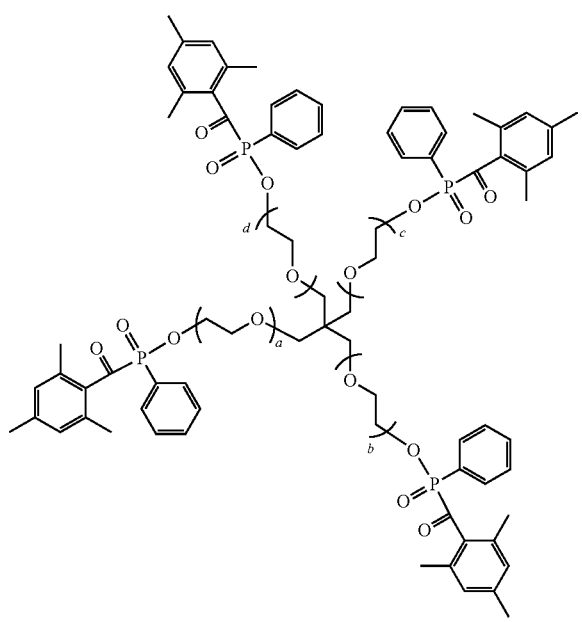

A solution of 100 ml of toluene, 3.49 g of triethylamine and 5.31 g of phenyl(2,4,6-trimethylbenzoyl)phosphinic chloride was heated to 70° C. under nitrogen atmosphere. 1 g of Polyol 4640 (ethoxylathed pentaeritritol, Perstorp Specialty Chemicals A.B.) was added and the solution stirred for 1.5 hours. The reaction mixture was cooled to room temperature and 100 ml of deionized water were added. The organic phase was separated, washed once with 100 ml of a saturated water solution of NaHCO$_3$ and twice with 100 ml of water and finally dried over Na$_2$SO$_4$. The solvent was removed under reduced pressure obtaining 2.8 g of photoinitiator, as a viscous liquid.

$^1$H-NMR (CDCl$_3$, δ ppm): 2.00-2 (m, 24H), 2.15-2.25 (m, 12H), 3.23-3.72 (m, 19H), 3.95-4.30 (m, 8H), 6.72-6.82 (m, 8H), 7.38-7.65 (m, 12H), 7.70-7.89 (m, 8H)

$^{31}$P-NMR (CDCl$_3$, δ ppm): 18.2

Example 5

Preparation of PI-2:

A solution of 25 ml of toluene, 4.18 ml of triethylamine and 3.5 g of phenyl(2,4,6-trimethylbenzoyl)phosphinic chloride was heated to 50° C. under nitrogen atmosphere. 0.54 g of trimethylolpropane were added and the solution was stirred for one hour. The reaction mixture was cooled to room temperature and 10 ml of deionized water were added. The organic phase was separated, washed once with 20 ml of a saturated water solution of NaHCO$_3$ and twice with 20 ml of water and finally dried over Na$_2$SO$_4$. The solvent was removed under reduced pressure. The reaction product was purified by flash column chromatography on silica gel (toluene/ethyl acetate 6:4) obtaining 1.5 g of photoinitiator, as a viscous liquid.

$^1$H-NMR (CDCl$_3$, δ ppm): 0.2-0.3 (m, 3H), 1.19-1.38 (m, 2H), 2.02-2.11 (m, 18H), 2.28-2.38 (m, 9H), 3.88-4.06 (m, 6H), 6.70-6.80 (m, 6H), 7.36-7.54 (m, 9H), 7.73-7.88 (m, 6H)

Example 6

Preparation of PI-7:

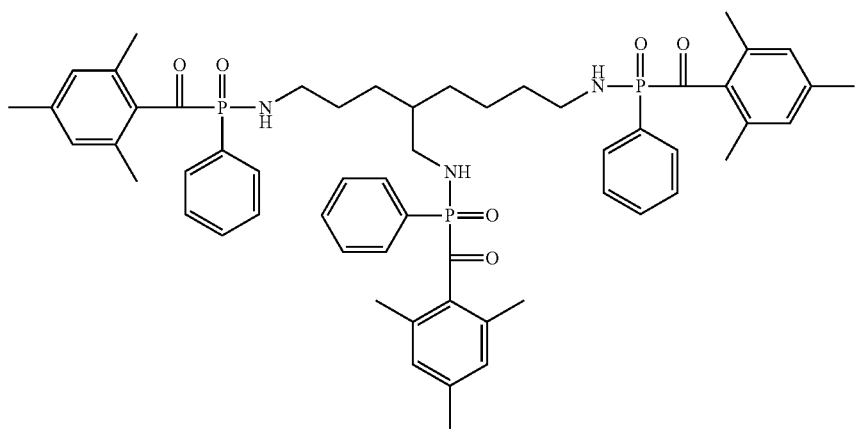

A solution of 100 ml of toluene, 3.49 g of triethylamine and 5.31 g of phenyl(2,4,6-trimethylbenzoyl)phosphinic chloride was stirred at room temperature under nitrogen atmosphere. 0.8 g of 4-aminomethyl-1,8-octanediamine (Ascend Performance Materials LLC, USA) was added and the solution stirred for 1.5 hours. At the end of the reaction, 100 ml of deionized water were added, the organic phase was separated and washed once with 100 ml of a saturated water solution of NaHCO$_3$ and twice with 100 ml of water. The organic solution was then dried over Na$_2$SO$_4$ and the solvent was removed under reduced pressure. The reaction product was purified by flash column chromatography on silica gel (dichloromethane/methanol 95:5) obtaining 1 g of photoinitiator, as a viscous liquid.

$^1$H-NMR (CDCl$_3$, δ ppm): 0.9-1.72 (m, 11H), 1.90-2.04 (m, 12H), 2.16-2.25 (m, 9H), 2.78-3.52 (m, 6H), 6.56-6.68 (m, 6H), 7.26-7.88 (m, 15H)

Example 7

Preparation of PI-13:

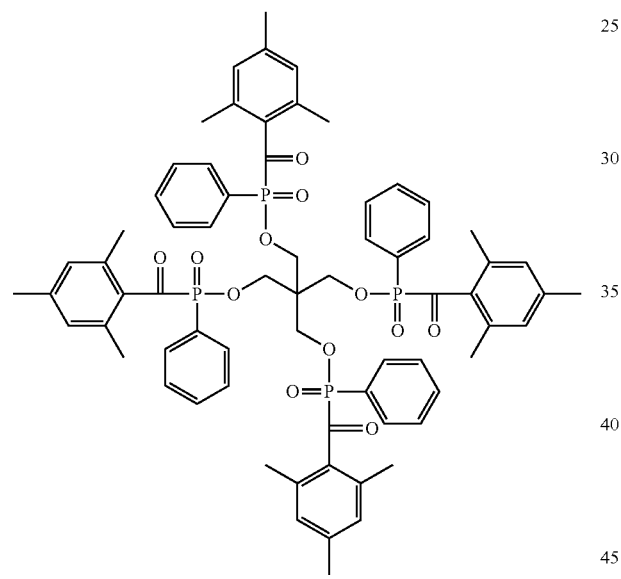

A solution of 25 ml of toluene, 2.44 g of triethylamine and 3.5 g of phenyl(2,4,6-trimethylbenzoyl)phosphinic chloride was heated to 60° C. under nitrogen atmosphere. 0.5 g of pentaerytrithol were added and the solution stirred for one hour. The reaction mixture was cooled to room temperature and 10 ml of deionized water were added. The organic phase was separated, washed once with 20 ml of a saturated water solution of NaHCO$_3$ and twice with 20 ml of water and finally dried over Na$_2$SO$_4$. The solvent was removed under reduced pressure. The reaction product was purified by flash column chromatography on silica gel (toluene/ethyl acetate 6:4; Retention factor (Rf) 0.7), obtaining 0.3 g of photoinitiator, as a viscous liquid.

$^1$H-NMR (CDCl$_3$, δ ppm): 1.85-1.96 (m, 24H), 2.05-2.11 (m, 12H), 4.02-4.12 (m, 8H), 6.56-6.66 (m, 8H), 7.21-7.51 (m, 12H), 7.59-7.61 (m, 8H)

Example 8

Preparation of PI-16:

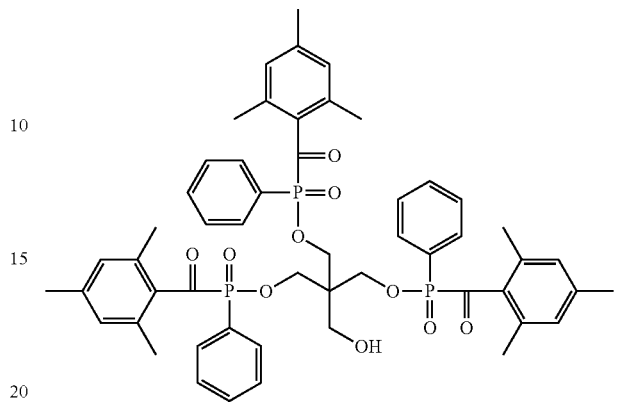

The photoinitiator was prepared following the same procedure of Example 7. The reaction product was purified by flash column chromatography on silica gel (toluene/ethyl acetate 6:4; Rf 0.3) obtaining 0.5 g of photoinitiator, as a viscous liquid.

$^1$H-NMR (CDCl$_3$, δ ppm): 1.88-2.00 (m, 18H), 2.05-2.08 (m, 9H), 3.20 (s, 2H), 3.82-4.00 (m, 6H), 6.58-6.70 (m, 6H), 7.24-7.40 (m, 6H), 7.40-7.54 (m, 3H), 7.60-7.75 (m, 6H)

Example 9

Preparation of PI-8:

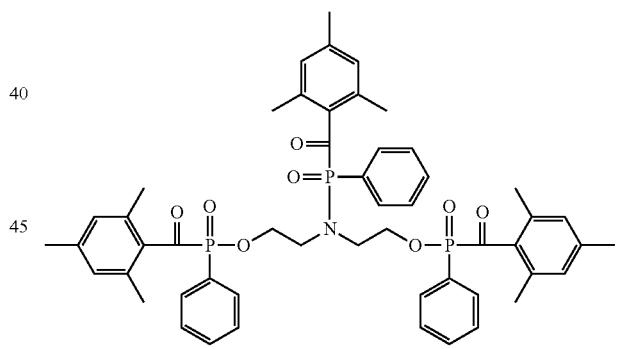

A solution of 150 ml of dichloromethane, 3.49 g of triethylamine and 5.31 g of phenyl(2,4,6-trimethylbenzoyl) phosphinic chloride was heated to 50° C. under nitrogen atmosphere. 0.4 g of diethanolamine were added and the solution was stirred for 2 hours. The reaction mixture was cooled to room temperature and 10 ml of deionized water were added. The organic phase was separated, washed three times with 100 ml of a saturated water solution of NaHCO$_3$ and twice with 100 ml of water and finally dried over Na$_2$SO$_4$. The solvent evaporated under reduced pressure. The reaction product was purified by flash column chromatography on silica gel (dichloromethane/methanol 9:1), obtaining 0.5 g of photoinitiator, as a viscous liquid.

$^1$H-NMR (CDCl$_3$, δ ppm): 1.98 (s, 18H), 2.14 (s, 9H), 3.08-3.22 (m, 4H), 3.97-4.15 (m, 4H), 6.68 (s, 6H), 7.27-7.39 (m, 6H), 7.41-7.51 (m, 3H), 7.61-7.76 (m, 6H).

Example 10

Preparation of PI-17 (Wherein a+b+c is About 7):

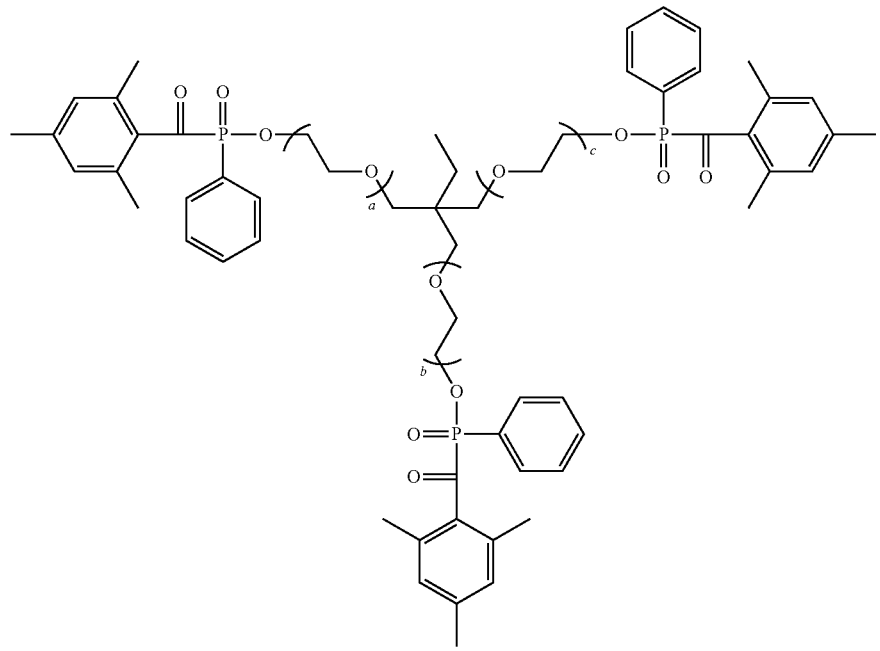

A solution of 150 ml of dichloromethane, 10.5 g of triethylamine and 15 g of phenyl(2,4,6-trimethylbenzoyl)phosphinic chloride was heated to 50° C. under nitrogen atmosphere. 5 g of Perstorp 3380 (ethoxylated trimethylolpropane, Perstorp Specialty Chemicals A.B.) were added and the solution was stirred for 2 hours. The reaction mixture was cooled to room temperature and 200 ml of deionized water were added. The organic phase was separated, washed three times with 200 ml of a saturated water solution of NaHCO$_3$ and twice with 200 ml of water and dried over Na$_2$SO$_4$. The solvent was removed under reduced pressure and the product was purified by flash column chromatography on silica gel (dichloromethane/methanol 97:3), obtaining 7.35 g of photoinitiator, as a viscous liquid.

$^1$H-NMR (CDCl$_3$, δ ppm): 0.64-0.82 (m, 3H), 1.20-1.38 (m, 2H), 2.02 (s, 18H), 2.19 (s, 9H), 3.11-3.63 (m, 30H), 3.80-4.6 (m, 7H), 6.72 (s, 6H), 7.32-7.58 (m, 9H), 7.68-7.82 (m, 6H)

Example 11

Preparation of PI-12 (Wherein a+b+c is About 8.5):

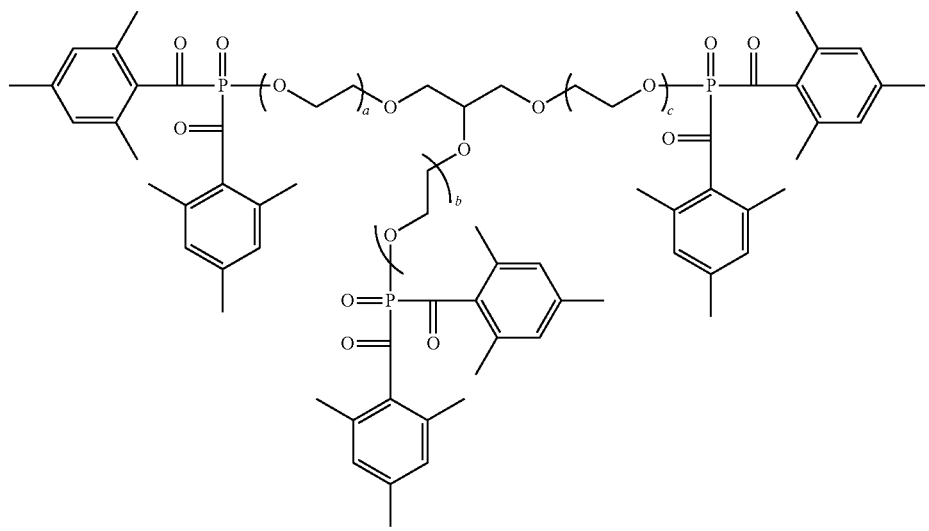

A solution of 10 ml of dichloromethane, 56.67 mg of triethylamine and 210 mg of Bis(2,4,6-trimethylbenzoyl)phosphinic chloride (prepared according to WO2014/095724 (BASF A.G.)) was warmed to 50° C. under nitrogen atmosphere. 86 mg of Aionico GL/609 were added and the solution was stirred for one hour. The reaction mixture was cooled to room temperature and 5 ml of deionized water were added. The organic phase was separated and washed once with 5 ml of a saturated water solution of $NaHCO_3$ and twice with 5 ml of water, dried over $Na_2SO_4$ and the solvent evaporated under reduced pressure. The product was purified by flash column chromatography on silica gel (Dichloromethane/Methanol 9:1) obtaining 0.1 g of photoinitiator.

$^1$H-NMR (CDCl$_3$, δ ppm): 2.15 (s, 18H), 2.26 (s, 36H), 3.42-3.89 (m, 40H), 6.72 (s, 12H)

Performance Test

Clear Formulation

The photocurable compositions according to the invention were prepared dissolving the photoinitiators of Examples 1-6 and 10 at a concentration of 4% wt in a mixture 99.5:0.5 w/w of Ebecryl 605 and Ebecryl 350 (Allnex).

A photocurable composition comprising 4% wt of Lucirin TPO-L (BASF AG) was used as comparative Example.

Each photocurable composition, placed in the sample lodgment of a FT-IR spectrophotometer (FT-IR 430-Jasco), was exposed to different light sources (160 W mercury lamp and 9000 mW/cm$^2$ LED emitting at 400 nm) set at a distance of 65 mm from the sample and at an angle of 30°. IR spectra were acquired at constant time intervals during the exposition and the reduction over the time of the peak area at 1408 cm$^{-1}$, assigned to the acrylic double bond, was determined using the IR software. This allows to quantify the degree of polymerization and therefore the efficiency of the photoinitiator.

Table 2 reports the % of polymerization over the time. Table 3 reports the % of polymerization over the time corrected for the number of photoactive groups in each formulation.

TABLE 2

| Photoinitiator | Mercury Lamp after 0.2" | Mercury Lamp after 1" | LED 400 nm after 0.5" | LED 400 nm after 2" |
|---|---|---|---|---|
| Lucirin TPO-L* | 61 | 63 | 60 | 62 |
| Example 1 | 57 | 58 | 55 | 55 |
| Example 2 | 62 | 64 | 61 | 62 |
| Example 3 | 64 | 67 | 54 | 56 |
| Example 4 | 58 | 59 | 54 | 55 |
| Example 5 | 62 | 63 | 49 | 50 |
| Example 6 | 39 | 41 | 46 | 47 |
| Example 10 | 63 | 64 | 63 | 64 |

*Comparative

TABLE 3

| Photoinitiator | Mercury Lamp after 0.2" | Mercury Lamp after 1" | LED 400 nm after 0.5" | LED 400 nm after 2" |
|---|---|---|---|---|
| Lucirin TPO-L* | 61 | 63 | 60 | 62 |
| Example 1 | 71 | 72 | 68 | 68 |
| Example 2 | 84 | 86 | 82 | 84 |
| Example 3 | 92 | 96 | 77 | 80 |
| Example 4 | 66 | 67 | 62 | 63 |
| Example 5 | 62 | 63 | 49 | 50 |
| Example 6 | 41 | 43 | 48 | 49 |
| Example 10 | 83 | 84 | 83 | 84 |

*Comparative

The results of Tables 2 and 3 demonstrate the high reactivity of the multifunctional mono- and bis-acylphosphine oxides of the invention, in particular considering the reactivity per photoactive group (Table 3). These performances can be compared with those of photoinitiators of the prior art reported in US2012/0046376 (Table 8 and 9), U.S. Pat. No. 7,166,647 (Table 1) and U.S. Pat. No. 7,354,957 (col. 14 lines 44-54), and also in *Macromol. Chem. Phys.* 208, 2007, 1694-1706 (Tables 4 and 5) and *J. Photochem. Photobio. A: Chem.* 159, 2003, 103-114 (Table 5).

Pigmented Cyan Compositions

The photocurable compositions for the test were prepared by dissolving the photoinitiators of Example 1-5 at a concentration of 5.0% wt each in a cyan ink for ink-jet printing.

A photocurable composition comprising 5% wt of Lucirin TPO-L (BASF A.G.) was used as comparative Example.

The photocurable compositions, placed in the sample lodgment of a spectrophotometer FT-IR (FT-IR 430-Jasco), were exposed to a LED source (400 nm, 9000 mW/cm$^2$) located at a distance of 65 mm from the sample and at an angle of 30°.

IR spectra were acquired at constant time intervals during the exposition and the reduction over the time of the area of the peaks at 1408 cm$^{-1}$ assigned to the acrylic double bond was determined using the IR software. This allows to quantify the degree of polymerization and therefore the efficiency of the photoinitiator.

The results, expressed as % of polymerization over the time, are reported in Table 4.

TABLE 4

| Photoinitiator | after 0.5" | after 2" |
|---|---|---|
| Lucirin TPO-L* | 13 | 29 |
| Example 1 | 12 | 26 |
| Example 2 | 18 | 34 |
| Example 3 | 6 | 10 |
| Example 4 | 12 | 26 |
| Example 5 | 15 | 32 |

*Comparative

Pigmented White Compositions

The photocurable compositions for the test were prepared by dissolving the photoinitiators of Example 1-5 at a concentration of 6.0% wt each in a white pigmented system comprising unsaturated polystyrene diluted with styrol and 20% wt of titanium dioxide.

The resulting compositions were homogenized with a mechanical stirrer and applied on a glass substrate (20×10 cm) with a thickness of 100 μm by means of film applicator (Erichsen, Quadruple Film Applicator, Model 360). The solvent was removed by flashing-off at 30° C. for 5 min and then the film was exposed to an gallium lamp (120 W/cm) with a line speed of 10 m/min.

A photocurable white composition comprising 6% wt of Lucirin TPO-L (BASF A.G.) was used as comparative Example.

The performances of the photoinitiators were evaluated by determining the hardness according to the standard method ASTM D4366 (Konig Pendulum) and the colour stability, according to the White Berger Index, using a Color Guide 45/0 (BYK).

Before the performance determination, the cured films were conditioned in the dark for 12 hours at room temperature.

The results are reported in Table 5.

TABLE 5

| Photoinitiator | Hardness (sec.) | White Index |
|---|---|---|
| Lucirin TPO-L* | 158 | 75.8 |
| Example 1 | 147 | 79.4 |
| Example 2 | 141 | 79.0 |
| Example 3 | 120 | 74.8 |
| Example 4 | 143 | 79.5 |
| Example 5 | 165 | 75.8 |

*Comparative

The multifunctional mono- and bis-acylphosphine oxides of the invention show a reactivity comparable or higher to Lucirin TPO-L, also in pigmented compositions. They also show a colour stability (no yellowing) comparable to the monofunctional photoinitiator.

The invention claimed is:

1. Photoinitiators of formula I:

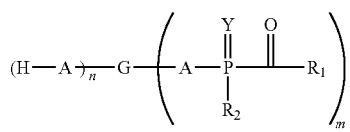

wherein:
each said A represents independently of one another O, S, or $NR_3$;
said G is a residue of multifunctional compound G-(A-H)$_{m+n}$, wherein each said A-H represents an alcohol, amino or thiol group;
said m and said n are both integer numbers and m+n has a value in the range of 3 to 10;
said m has a value ranging from 3 to 8;
each said $R_1$ represents, independently of one another, $C_1$-$C_{18}$ alkyl, $C_6$-$C_{12}$ aryl or $C_5$-$C_{12}$ cycloalkyl, each of which is uninterrupted or interrupted by one or more oxygen and/or sulfur atoms and/or one or more substituted or unsubstituted imino groups, or is a five- to six-membered heterocyclic radical containing oxygen and/or nitrogen and/or sulfur atoms, wherein said radical may be substituted by aryl, alkyl, aryloxy, alkoxy, heteroatoms and/or heterocyclic radicals;
each said $R_2$ represents, independently of one another $R_1$—(C═O)—, $C_1$-$C_{18}$ alkyl, $C_6$-$C_{12}$ aryl or $C_5$-$C_{12}$ cycloalkyl, each of which is uninterrupted or interrupted by one or more oxygen and/or sulfur atoms and/or one or more substituted or unsubstituted imino groups, or is a five- to six-membered heterocyclic radical containing oxygen and/or nitrogen and/or sulfur atoms, where said radical may be substituted by aryl, alkyl, aryloxy, alkoxy, heteroatoms and/or heterocyclic radicals;
said Y is O or S; and
said $R_3$ is hydrogen or $C_1$-$C_4$ alkyl;
provided that the photoinitiators of formula I do not contain photocurable ethylenically unsaturated groups.

2. The photoinitiators of claim 1, wherein said m+n has a value within a range of 3 to 8.

3. The photoinitiators of claim 1, wherein said m has a value within a range of 3 to 6.

4. The photoinitiators of claim 1, wherein said $R_1$ is selected from the group consisting of phenyl, 2,6-dichlorophenyl, 2,4,6-trichlorophenyl, 2,6-dimethylphenyl, 2,4,6-trimethylphenyl, 2,6-diethylphenyl, 2,6-dimethoxyphenyl, 2,6-diethoxyphenyl, α-naphthyl, 2,6-dinitrophenyl, 2,6-dimethylcyclohexyl, 2,6-diethylcyclohexyl, 2,6-dimethoxycyclohexyl, 2,6-diethoxycyclohexyl, 2,6-dichlorocyclohexyl, tert-butyl, pentyl, hexyl, heptyl, octyl and 2-ethylhexyl.

5. The photoinitiators of claim 1, wherein said $R_2$ is selected from the group consisting of $R_1$—(C═O)—, methyl, ethyl, propyl, isopropyl, n-butyl, sec-butyl, tert-butyl, pentyl, hexyl, 2-ethylhexyl, phenyl, xylyl, 4-biphenylyl, 2-, 3- or 4-chlorophenyl, 2,4-dichlorophenyl, 2-, 3- or 4-methylphenyl, 2,4-dimethylphenyl, 2-, 3- or 4-ethylphenyl, 2-, 3- or 4-methoxyphenyl, 2,4-dimethoxyphenyl, 2-, 3- or 4-ethoxyphenyl, α-naphthyl, methylnaphthyl, chloronaphthyl, ethoxynaphthyl and 2- or 4-nitrophenyl.

6. The photoinitiators of claim 1, wherein said G-(A-H)$_{m+n}$ is selected from the group consisting of monomeric polyols, oligomeric polyols, polymeric polyol and a mixture thereof.

7. A photocurable composition comprising:
a) from 0.05 to 20% by weight of at least one photoinitiator of formula I;

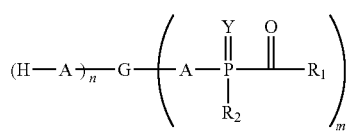

wherein said A, G, m, n, $R_1$, $R_2$, Y and $R_3$ do not contain photocurable ethylenically unsaturated groups;
each said A represents independently of one another O, S, or $NR_3$;
said G is a residue of multifunctional compound G-(A-H)$_{m+n}$, wherein each said A-H represents an alcohol, amino or thiol group;
said m and said n are both integer numbers and m+n has a value in the range of 3 to 10;
said m has a value ranging from 3 to 8;
each said $R_1$ represents, independently of one another, $C_1$-$C_{18}$ alkyl, $C_6$-$C_{12}$ aryl and $C_5$-$C_{12}$ cycloalkyl, each of which is uninterrupted or interrupted by one or more oxygen and/or sulfur atoms and/or one or more substituted or unsubstituted imino groups, or are a five- to six-membered heterocyclic radical containing oxygen and/or nitrogen and/or sulfur atoms, wherein said radical may be substituted by aryl, alkyl, aryloxy, alkoxy, heteroatoms and/or heterocyclic radicals;
each said $R_2$ represents, independently of one another $R_1$—(C═O)—, or one of $C_1$-$C_{18}$ alkyl, $C_6$-$C_{12}$ aryl and $C_5$-$C_{12}$ cycloalkyl, each of which is uninterrupted or interrupted by one or more oxygen and/or sulfur atoms and/or one or more substituted or unsubstituted imino groups, or is a five- to six-membered heterocyclic radical containing oxygen and/or nitrogen and/or sulfur atoms, where said radical may be substituted by aryl, alkyl, aryloxy, alkoxy, heteroatoms and/or heterocyclic radicals;

said Y is O or S; and
said $R_3$ is hydrogen or $C_1$-$C_4$ alkyl; and
   b) from 30 to 99.9% by weight of at least one ethylenically unsaturated compound.

8. The photocurable composition of claim 7, wherein said photocurable composition comprises from 0.2 to 10% by weight of said at least of said photoinitiator of formula I and from 50 to 98.9 by weight of said at least one ethylenically unsaturated compound.

9. The photocurable composition of claim 7, further comprising c) from 0.5 to 15% by weight of a further photoinitiator.

10. The photocurable composition of claim 7, further comprising c) from 0.05 to 12% by weight of a photosensitizer.

11. Photoinitiators of formula I:

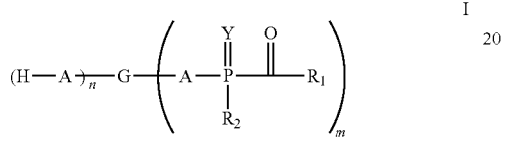

I wherein:
each said A represents independently of one another O, S, or $NR_3$;
said G is a residue of multifunctional compound G-(A-H)$_{m+n}$, wherein each said A-H represents an alcohol, amino or thiol group;
said m and said n are both integer numbers and m+n has a value in the range of 3 to 10;
said m has a value ranging from 3 to 8;
each said $R_1$ represents, independently of one another, $C_1$-$C_{18}$ alkyl, $C_6$-$C_{12}$ aryl or $C_5$-$C_{12}$ cycloalkyl, which may be substituted by aryl, alkyl, aryloxy, alkoxy, heteroatoms and/or heterocyclic radicals;
each said $R_2$ represents, independently of one another $R_1$—(C═O)—, $C_1$-$C_{18}$ alkyl, $C_6$-$C_{12}$ aryl or $C_5$-$C_{12}$ cycloalkyl, which may be substituted by aryl, alkyl, aryloxy, alkoxy, heteroatoms and/or heterocyclic radicals;
said Y is O or S; and
said $R_3$ is hydrogen or $C_1$-$C_4$ alkyl;
wherein the photoinitiators of formula I do not contain photocurable ethylenically unsaturated groups.

* * * * *